US007608242B2

(12) United States Patent
Cuthbertson et al.

(10) Patent No.: US 7,608,242 B2
(45) Date of Patent: Oct. 27, 2009

(54) PEPTIDE-CHELATE CONJUGATES

(75) Inventors: Alan Cuthbertson, Oslo (NO); Marivi Mendizabal, Amersham (GB); Mark Dixon, Southampton (GB); Anthony E. Storey, Amersham (GB); Edward R. Bacon, Westchester, PA (US); Vinay Chandrakant Desai, Lafayette, NJ (US); Sudhakar Kasina, Seattle, WA (US); Henry Raphael Wolfe, Exton, PA (US)

(73) Assignee: GE Healthcare Limited, Buckinghamshire (GB)

( * ) Notice: Subject to any disclaimer, the term of this patent is extended or adjusted under 35 U.S.C. 154(b) by 965 days.

(21) Appl. No.: 10/469,801

(22) PCT Filed: Mar. 1, 2002

(86) PCT No.: PCT/GB02/00857

§ 371 (c)(1), (2), (4) Date: Dec. 10, 2004

(87) PCT Pub. No.: WO02/070018

PCT Pub. Date: Sep. 12, 2002

(65) Prior Publication Data
US 2006/0222593 A1    Oct. 5, 2006

(30) Foreign Application Priority Data
Mar. 2, 2001 (GB) ................ 0105224.0

(51) Int. Cl.
*A61K 51/00*  (2006.01)
*A61M 36/14*  (2006.01)

(52) U.S. Cl. .............. 424/1.69; 514/10; 530/317; 424/1.11; 424/1.65; 534/14

(58) Field of Classification Search ............. 424/1.11, 424/1.65, 1.69, 9.1, 9.3, 9.4, 9.5, 9.6, 9.7; 534/7, 10–16; 530/300, 317; 514/10
See application file for complete search history.

(56) References Cited

U.S. PATENT DOCUMENTS 5,242,679 A * 9/1993 Fritzberg et al. .......... 424/1.53
6,007,792 A    12/1999 Dean et al.

FOREIGN PATENT DOCUMENTS

| WO | WO95/00553 | | 1/1995 |
| WO | WO95/11694 | | 5/1995 |
| WO | WO97/10852 | | 3/1997 |
| WO | WO 9921587 | * | 5/1999 |
| WO | WO-99/21587 | * | 6/1999 |

OTHER PUBLICATIONS

Kwamena E. Baidoo, et.al. "Synthesis of A Diaminedithiol Bifunctional Chelating agent for Incorporation of Technetium-99M Into Biomolecules", Bioconjugate Chemistry, American Chemical Society, Wash. US vol. 1, No. 2, 1990, pp. 132-137, XP000371813.

* cited by examiner

*Primary Examiner*—D L Jones
(74) *Attorney, Agent, or Firm*—Craig Bohlken

(57) ABSTRACT

A peptide-chelate conjugate with affinity for the ST receptor is disclosed, wherein the chelate is tetradentate. The peptide-chelate conjugate of the invention may be labelled with a radiometal to provide a metal complex. A radiopharmaceutical composition comprising the metal complex is provided, which is suitable for the diagnostic imaging of colorectal cancer. Also provided for in the invention is a kit for the preparation of the radiopharmaceutical preparation.

15 Claims, 10 Drawing Sheets

SEQUENCE LISTING

<160> NUMBER OF SEQ ID NOS: 8

<210> SEQ ID NO 1
<211> LENGTH: 14

```
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

Cys Cys Glu Leu Cys Cys Asn Pro Ala Cys Ala Gly Cys Tyr
1               5                   10

<210> SEQ ID NO 2
<211> LENGTH: 16
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 2

Asn Ser Ser Asn Tyr Cys Glu Leu Cys Cys Asn Pro Ala Cys Gly Cys
1               5                   10                  15

<210> SEQ ID NO 3
<211> LENGTH: 21
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 3

Glu Glu Glu Glu Glu Glu Gly Cys Cys Glu Leu Cys Cys Asn Pro Ala
1               5                   10                  15

Cys Ala Gly Cys Tyr
            20

<210> SEQ ID NO 4
<211> LENGTH: 21
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 4

Lys Lys Lys Lys Lys Lys Gly Cys Cys Glu Leu Cys Cys Asn Pro Ala
1               5                   10                  15

Cys Ala Gly Cys Thr
            20

<210> SEQ ID NO 5
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE
<220> FEATURE:
<221> NAME/KEY: misc_feature
<222> LOCATION: (4)..(6)
<223> OTHER INFORMATION: GLUTAMIC ACID

<400> SEQUENCE: 5

Gly Gly Gly Glu Glu Glu Cys Cys Glu Leu Cys Cys Asn Pro Ala Cys
1               5                   10                  15

Ala Gly Cys Tyr
            20

<210> SEQ ID NO 6
<211> LENGTH: 19
<212> TYPE: PRT
```

-continued

```
<213> ORGANISM: ARTIFICIAL SEQUENCE
<220> FEATURE:
<223> OTHER INFORMATION: SYNTHETIC PEPTIDE
<220> FEATURE:
<221> NAME/KEY: misc_feature
<222> LOCATION: (4)..(5)
<223> OTHER INFORMATION: X INDICATES AMINOCAPROIC ACID

<400> SEQUENCE: 6

Gly Gly Gly Xaa Xaa Cys Cys Glu Leu Cys Cys Asn Pro Ala Cys Ala
1               5                   10                  15

Gly Cys Tyr

<210> SEQ ID NO 7
<211> LENGTH: 13
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 7

Cys Cys Glu Leu Cys Cys Asn Pro Ala Cys Ala Gly Cys
1               5                   10

<210> SEQ ID NO 8
<211> LENGTH: 14
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 8

Ala Ala Glu Leu Ala Ala Asn Pro Ala Ala Ala Gly Ala Tyr
1               5                   10
```

PEPTIDE-CHELATE CONJUGATES

This application is a filing under 35 U.S.C. § 371 and claims priority to international application number PCT/GB02/00857 filed Mar. 1, 2002. This application also claims priority to application No. 0105224.0 filed Mar. 2, 2001, in Great Britain

FIELD OF THE INVENTION

This invention relates to radiopharmaceuticals, in particular the invention relates to a peptide-chelate conjugate, comprising a peptide with affinity for the ST receptor. The compound of the invention is suitable for diagnostic imaging of colorectal cancer in a mammal.

The invention additionally relates to a radiolabelled peptide-chelate conjugate with affinity for the ST receptor, wherein radiolabelling of the peptide-chelate conjugate does not interfere with the affinity of the peptide for the ST receptor. In another aspect of the invention, use of such a compound for imaging of cancer of colorectal origin is provided.

A kit for the production of a radiolabelled peptide-chelate conjugate for imaging colorectal cancer is also disclosed.

BACKGROUND ART

Colorectal carcinoma (CRC) is the fourth most common malignancy worldwide following cancers of the lung, breast and prostate. Metastases of CRC origin are the main cause of death in patients diagnosed with colorectal primary tumours. Approximately 150,000 to 200,000 new cases are diagnosed annually in the USA and around 50,000 deaths are attributed to this disease. Many patients die due to the metastatic spread of the disease with 60-80% of cases developing liver lesions during the illness. The positive identification of liver metastasis is therefore a clear indication of latent disease. Although much less common, other possible sites of spread include lung, brain and occasionally bone.

Due to the strong correlation between extent of liver involvement (number and location of metastasis) and resectability, the appropriate evaluation of patients regarding suitability for surgery is becoming more important (Liver Metastasis: Biology, diagnosis and treatment. Garden O. J., Gereghty J. G., Nagorney D. M. eds. 1998). The need for an agent capable of detecting metastasis of small size (<1 cm) will have a profound impact on the treatment and management of CRC patients. There is a need to specifically detect small (<1 cm) metastatic lesions in the liver. The early detection of number and location of metastatic lesions is critical. There is also a need to characterise and specifically identify the origin of the tumour with no interference from other possible lesions (e.g. cysts, benign lesions, non-treatable tumours).

A low-molecular weight heat-stable toxin is produced by enterotoxic strains of E. coli. This toxin, known as ST peptide, mediates acute diarrheal disease by binding to its receptor on colorectal cells and stimulating guanylate cyclase. Synthetic ST peptides that bind to the ST receptor without mediating acute diarrheal disease are disclosed in U.S. Pat. Nos. 4,545,931 and 4,886,663. These synthetically produced peptides are suitable for human administration for therapeutic and diagnostic purposes.

Targeted ligands directed towards receptors that are expressed selectively on tumour cells of colorectal origin are a means to specifically detect the presence of cancers of colorectal origin. Thus, the ST receptor is a potential target mechanism. Gastrointestinal mucosal cells specifically express the ST receptor and the expression persists after colonic and rectal mucosal cells undergo malignant neoplasic transformation. No ST peptide has been found in any other extra-intestinal tissues, therefore specificity of ligands to tissue of gastrointestinal origin is maintained. Similar levels of expression have been found in human primary and metastatic colorectal tissues with different grades of differentiation and location. A specific ligand for the ST receptor will only bind to metastatic disease, as access to the apical side of intestinal cells will be avoided if the compound is injected intravenously.

Radiolabelled ST peptides for CRC imaging and diagnosis have been previously documented. U.S. Pat. No. 5,518,888 claims radiodiagnostic agents based on ST peptides. In one embodiment of that invention, the peptides may be linked to a radioactive imaging agent, such as radioactive iodine, $^{111}$In or $^{99m}$Tc. $^{99m}$Tc is chelated by DTPA, which is converted to an anhydride and reacted with an ST peptide. No other chelates are disclosed in U.S. Pat. No. 5,518,888. Radiolabelling thus renders the peptides suitable for use in radioimaging metastasized colorectal cancers. U.S. Pat. No. 6,060,037 discloses a method of radioimaging metastatic CRC using such radiolabelled ST peptides. The detection of localised accumulation or aggregation of radioactivity following administration of radiolabelled ST peptide is indicative of the presence of cells with ST receptors. WO 99/21587 and WO 99/39748 also disclose radiolabelled ST peptides for diagnostic imaging. In WO 99/21587 the preferred classes of radiometal complexing agents are terpyridines and phenanthrolines. In WO 99/39748 the complexing agents comprise a macrocyclic oligo-2,6-pyridine-containing ring which is a derivative of a terpyridine, quaterpyridine, quinpyridine, or sexipyridine.

DESCRIPTION OF THE INVENTION

Figure 1:
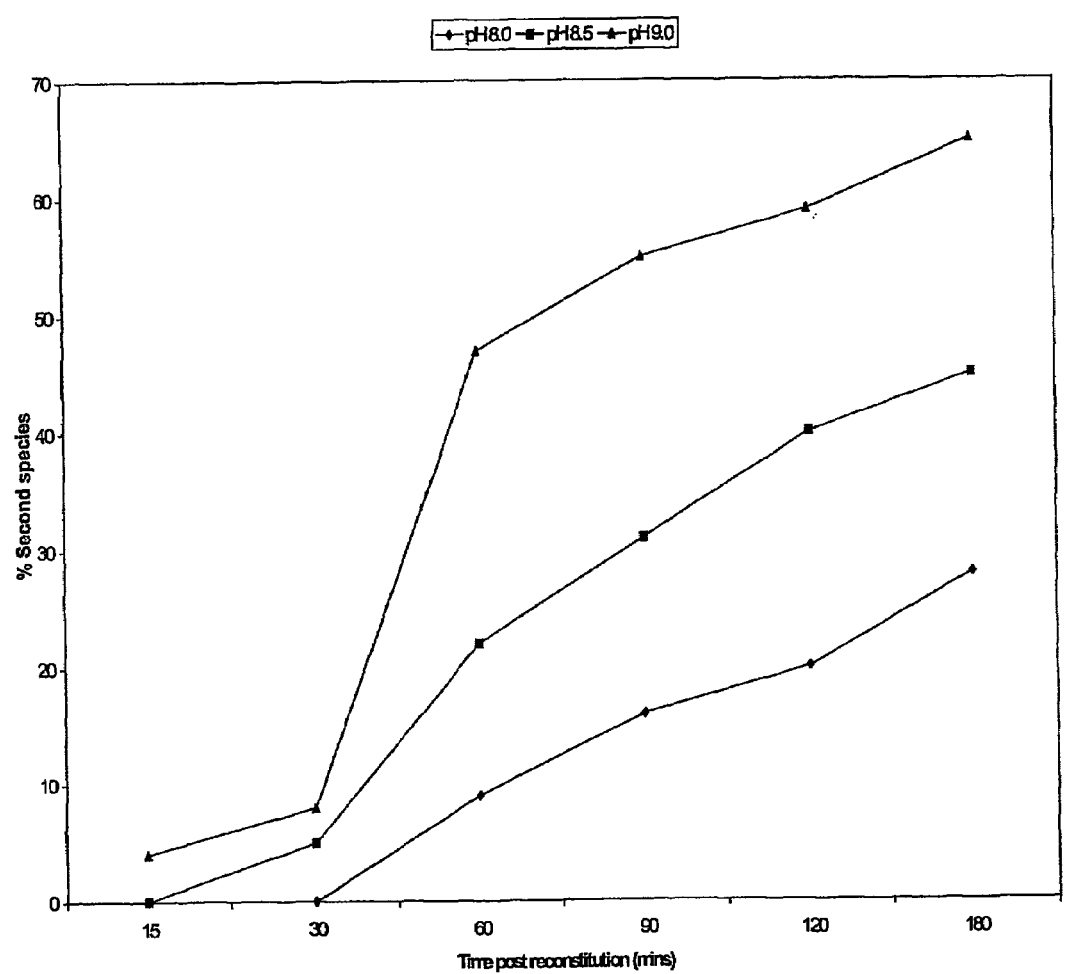
FIG. 1 shows the effect of pH 8.0, 8.5 and 9.0 in the radiolabelling reaction on the formation of Species 2 (CA-$ST_{5-18}$).

ST peptides are cyclic peptides containing three disulphide bonds. It has been found that these ST peptides are unstable under the basic pH conditions required for some $^{99m}$Tc chelator radiolabelling, giving in cleavage of the disulphide bridges and unacceptable loss of potency. This instability may rule out a large number of $^{99m}$Tc chelates that require pH ca. 8-9 for efficient labelling. Consequently, peptide-chelate conjugates would have to be labelled under acidic conditions to maintain high potency. However, such chelates need complicated labelling protocols and can generate $^{99m}$Tc-conjugates with poor efficacy, e.g., elevated hepatobiliary uptake and fast blood clearance. The present invention provides peptide-chelate conjugates that can be labelled under basic conditions without loss of potency of the ST peptide, to provide effective imaging agents.

In a first aspect, the present invention provides a peptide-chelate conjugate comprising a peptide having affinity for the ST receptor conjugated to a tetradentate chelating agent, wherein the peptide having affinity for the ST receptor comprises 10 to 25 amino acids. "A peptide having affinity for the ST receptor" is a biologically active peptide which is suitably between 10 and 25 amino acids, and preferably between 13 and 19 amino acids, derived from the ST peptide sequence, that binds the ST receptor with high affinity. The peptides of the present invention may be of naturally occurring or synthetic origin, but are preferably synthetic. These peptides may be conjugated directly to the chelate, or by means of a "linker group". "Linker groups" may comprise a peptide sequence of about 5 to 9 amino acids, with or without the inclusion of other groups such as aliphatic chains of up to 5 carbons in length. Preferred linker groups -poly-Lys-, -poly-Glu-, -(Gly)$_2$- Glu-(Lys)$_3$-, (Gly)$_2$-Glu-Lys-Glu-Lys-, (Phe)$_2$-(CH$_2$)$_5$—, (Lys)$_6$-Gly-, -(Gly)$_3$-(DGlu)$_3$- and -(Gly)$_3$-(aminocaproic acid)$_2$-. Labelled with a suitable radiometal, ST peptides of the invention are suitable for use as imaging agents to detect cancers of colorectal origin. Preferred peptides of the present invention are SEQ ID Nos. 1 and FF-(CH$_2$)$_5$-SEQ ID No. 7.

Especially preferred peptides having affinity for the ST receptor are SEQ ID Nos. 1 to 5, presented in the included sequence listing.

The negative control used in the experiments of the present invention is SEQ ID No. 8, i.e., SEQ ID No. 1 with all of the cysteines replaced with alanines and therefore lacking the disulphide bridges required for binding.

As used herein the term "tetradentate chelating agents" are chelates that are suitable for the formation of the peptide-chelate conjugates of the present invention, in which the radiometal is coordinated by the four metal donor atoms of the tetradentate chelating agent. A suitable radioactive metal ion is complexed by a tetradentate chelating agent by means of a donor set consisting of four metal donors which form at least one 5- or 6-membered chelate ring with the radiometal. Preferably, the tetradentate chelating agent forms 2 or more such 5- or 6-membered chelate rings with the radiometal. These ligands are particularly suitable for the complexation of technetium ($^{99m}$Tc), but may also be used for other radiometals.

The tetradentate chelating agent is present in the conjugate in order to produce a radiolabelled form of the peptide, suitable for diagnostic imaging. A suitable radioactive metal ion may be incorporated into the peptide-chelate conjugate by means of complexation with the tetradentate chelating agent. It is an important feature of the present invention that the potency of the ST peptide is not compromised by the process of radiolabelling.

Tetradentate chelating agents suitable for the present invention include but are not limited to the following:

(i) diaminedioximes of formula A:

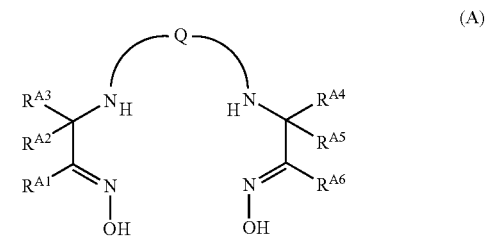

(A)

where $R^{A1}$-$R^{A6}$ are each independently an R group;

where R is H or $C_{1-10}$ alkyl, alkylaryl, alkoxyalkyl, hydroxyalkyl, fluoroalkyl, aminoalkyl or carboxyalkyl;

and Q is a bridging group of formula —(W)$_n$—;

where n is 3, 4 or 5 and each W is independently —O—, —NR— or —CR$_2$— provided that (W)$_n$ contains a maximum of one W group which is —O— or —NR—.

Preferred diaminedioximes have $R^{A1}$ to $R^{A6}$=C$_{1-3}$ alkyl, alkylaryl alkoxyalkyl, hydroxyalkyl, fluoroalkyl or aminoalkyl. Most preferred diaminedioximes have $R^{A1}$ to $R^{A6}$=CH$_3$.

(ii) N$_3$S ligands of formula B:

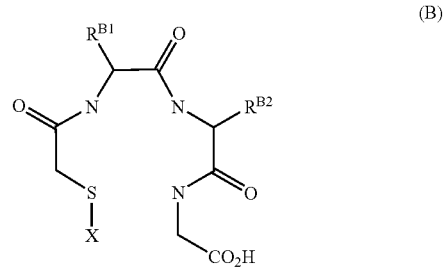

(B)

where X is a thiol protecting group such as benzoyl, acetyl or ethoxyethyl that is cleaved before or during the labelling process, and;

$R^{B1}$ and $R^{B2}$ may be H or the side chain of any amino acid, (iii) $N_4$ ligands of formula C:

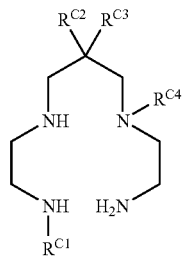

(C)

where $R^{C1}$—$R^{C4}$ may be H, alkyl, aryl or combinations thereof and where one of $R^{C1}$—$R^{C4}$ must be a functional group such as alkylamine, alkyl sulphide, alkoxy, alkyl carboxylate, alkyl arylamine or aryl sulphide. Ligands of this type include those with C=O amide linkages. Macrocyclic versions of formula C are also included, such as:

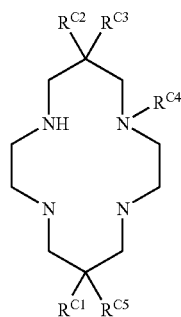

where $R^{C5}$ is as defined for $R^{C1}$ to $R^{C4}$, above.

(iv) Diaminediphenols of formula D:

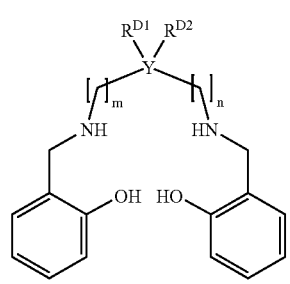

(D)

where Y is either C or N;

$R^{D1}$ and $R^{D2}$ may be either H, alkyl or aryl and where one of $R^{D1}$ and $R^{D2}$ must be a functional group such as alkylamine, alkyl sulphide, alkoxy, alkyl carboxylate, alkyl arylamine or aryl sulphide, and;

m=n=1 or 2.

(v) $N_2S_2$ ligands of formula E:

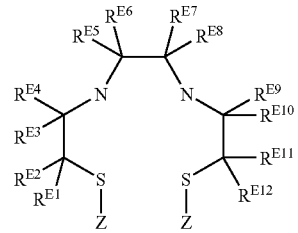

(E)

where Z is a thiol protecting group such as benzoyl, acetyl or ethoxyethyl that is cleaved before or during the labelling process, and;

$R^{E1}$—$R^{E12}$ may be each chosen from H, an aryl group or an alkyl group and where one of $R^{E1}$—$R^{E12}$ must be a functional group such as alkylamine, alkyl sulphide, alkoxy, alkyl carboxylate, alkyl arylamine or aryl sulphide, and;

one or more of the pairs $R^{E3}/R^{E4}$, $R^{E5}/R^{E6}$, $R^{E7}/R^{E8}$, $R^{E9}/R^{E10}$ may represent a C=O bond.

A preferred chelating agent of the present invention is a diaminedioxime of formula A, where $R^{A1}$—$R^{A6}$ are all $CH_3$, and Q is —$(CH_2)_2NR(CH_2)_2$—, where R is an R group as defined for Formula (A). A most preferred chelating agent is where R of —$(CH_2)_2NR(CH_2)_2$— is aminoalkyl, especially R=—$(CH_2)_2NH$—. The latter will be referred to in the remainder of this document as "chelating agent 1" (CA1). Another preferred chelating agent is an $N_3S$ ligand of formula B where $R^{B1}$ and $R^{B2}$ are both H and X is acetyl. This will be referred to as "chelating agent 2" (CA2) for the remainder of the document. "Chelating agent 3" (CA3) is an $N_3S$ ligand of formula B where $R^{B1}$ is $CH_2CH_2CH_2C$=O, $R^{B2}$ is H and X is ethoxyethyl.

The synthetic peptides of the present invention can be synthesised by solid phase methodology, as is well known in the art. A representative synthesis of $ST_{5-18}$ is given in Example 2. The peptide-chelate conjugates of the present invention can be prepared using bifunctional chelators, i.e., compounds in which the tetradentate chelator bears a pendant fictional group. Preferred functional groups are amino or carboxyl functional groups, which permit facile coupling via amide bonds to the amine or carboxyl groups on the peptides of interest, especially the amino- or carboxyl-terminus of the peptide.

$N_3S$ bifunctional chelators can be prepared by the method of Sudhaker et al [Bioconjugate Chem., Vol. 9, 108-117 (1998)]. The synthesis of diaminedioxime bifunctional chelators is described in Example 3. Diaminediphenol compounds can be prepared by the method of Pillai et al [Nucl. Med. Biol., Vol. 20, 211-216(1993)]. Bisamidedithiol compounds can be prepared by the method of Kung et al [Tetr. Lett., Vol 30, 4069-4072 (1989]. Monoamidemonoaminebisthiol compounds can be prepared by the method of Hansen et al [Inorg. Chem., Vol 38, 5351-5358 (1999)]. Functional tetraamines can be prepared by the method of Simon et al [J. Am. Chem. Soc., Vol 102, 7247 (1980)]. The critical processes in the synthesis of the CA1-$ST_{5-18}$ conjugate can be summarised as shown in Scheme 1 on the following page.

Conjugation of the peptide to the chelate is carried out prior to the labelling reaction. The direct method of conjugation is exemplified in the compound CA1-$ST_{5-18}$ (or CA1-SEQ ID No. 1). Conjugation via a linker molecule is exemplified in the compound CA1-$(Gly)_3$-$(D-Glu)_3$-$ST_{5-18}$ (or CA1-SEQ ID No. 5). Conjugations may be carried out via either the N-terminus or the C-terminus of the peptide molecule. Refer to Table I for these structures and structures of other suitable compounds of the present invention.

The compounds of the present invention have reproducibly high radiochemical purity (RCP), advantageous pharmacokinetics such as reduced gastrointestinal uptake, and imaging efficacy in tumoured animals. The compounds offer a distinct advantage over previously disclosed CRC-targeting compounds since they have improved pharmacokinetics and specific retention in tumour tissue compared to background tissues.

Scheme 1 Peptide assembly using automated peptide synthesiser

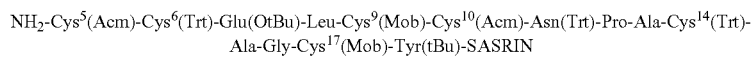

NH$_2$-Cys$^5$(Acm)-Cys$^6$(Trt)-Glu(OtBu)-Leu-Cys$^9$(Mob)-Cys$^{10}$(Acm)-Asn(Trt)-Pro-Ala-Cys$^{14}$(Trt)-Ala-Gly-Cys$^{17}$(Mob)-Tyr(tBu)-SASRIN

| Manual Coupling of Succinic anhydride and CA1 | 1) succinic anhydride<br>2) CA1; PyAOP/HOAt/NMM |
|---|---|

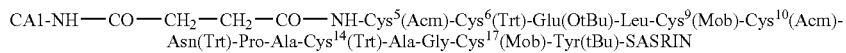

CA1-NH—CO—CH$_2$—CH$_2$—CO—NH-Cys$^5$(Acm)-Cys$^6$(Trt)-Glu(OtBu)-Leu-Cys$^9$(Mob)-Cys$^{10}$(Acm)-Asn(Trt)-Pro-Ala-Cys$^{14}$(Trt)-Ala-Gly-Cys$^{17}$(Mob)-Tyr(tBu)-SASRIN

| Cleavage of partially protected peptide from the solid-phase | 5% TIS in TFA; 30 min |
|---|---|

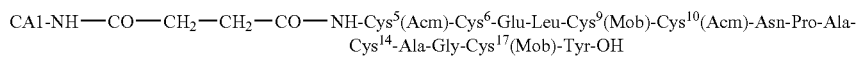

CA1-NH—CO—CH$_2$—CH$_2$—CO—NH-Cys$^5$(Acm)-Cys$^6$-Glu-Leu-Cys$^9$(Mob)-Cys$^{10}$(Acm)-Asn-Pro-Ala-Cys$^{14}$-Ala-Gly-Cys$^{17}$(Mob)-Tyr-OH

| Oxidation of the Cys6–Cys14<br>Disulphide-Purification | aq. K$_3$Fe(CN)$_6$; pH 8; 16h RT |
|---|---|

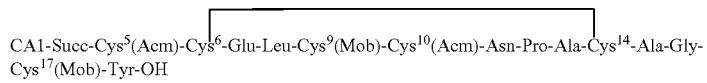

CA1-Succ-Cys$^5$(Acm)-Cys$^6$-Glu-Leu-Cys$^9$(Mob)-Cys$^{10}$(Acm)-Asn-Pro-Ala-Cys$^{14}$-Ala-Gly-Cys$^{17}$(Mob)-Tyr-OH

| Oxidation of the Cys5–Cys10<br>Disulphide-Purification | I$_2$; DMSO:AcOH (1:1); RT; 30 min |
|---|---|

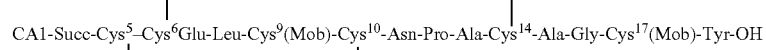

CA1-Succ-Cys$^5$-Cys$^6$-Glu-Leu-Cys$^9$(Mob)-Cys$^{10}$-Asn-Pro-Ala-Cys$^{14}$-Ala-Gly-Cys$^{17}$(Mob)-Tyr-OH

| Oxidation of the Cys9–Cys17<br>Disulphide-Purification | TFA/DMSO (90:10); RT; 15 min |
|---|---|

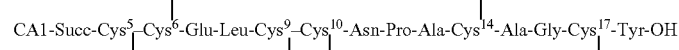

CA1-Succ-Cys$^5$-Cys$^6$-Glu-Leu-Cys$^9$-Cys$^{10}$-Asn-Pro-Ala-Cys$^{14}$-Ala-Gly-Cys$^{17}$-Tyr-OH Final purification and salt exchange Abbreviations

| Acm | = acetamidomethyl | HOAt | = |
|---|---|---|---|
| Trt | = trityl | NMM | = N-methylmorpholine |
| Mob | = 4-methoxybenzyl | TIS | = triisopropylsilane |
| RT | = room temperature | DMSO | = dimethylsulphoxide |
| TFA | = trifluoroacetic acid | AcOH | = acetic acid |
| PyAOP | = [7-Azabenzotriazol-1-yloxytris(pyrrolidino)phosphonium-hexafluorophosphate] | | |
| SASRIN | = super acid sensitive resin | | |

In a second aspect, the present invention provides a metal complex comprising a radiometal complexed to the tetradentate chelating agent of the peptide-chelate conjugate. Preferred chelating agents for the metal complex are chosen from diaminedioximes of formula A where $R^{41}$—$R^{46}$ are all $CH_3$ and Q is —$(CH_2)_2NR(CH_2)_2$—. An especially preferred diaminedioxime of formula A is CA1, as defined above. Other preferred chelating agents for the metal complex are the $N_3S$ ligands CA2 and CA3, defined above. A suitable radiometal may be chosen from positron emitters such as $^{64}Cu$ and $^{65}Cu$, or from gamma emitters such as $^{99m}Tc$. A preferred embodiment of the invention is a peptide-chelate conjugate radiolabelled with $^{99m}Tc$. A peptide-chelate conjugate radiolabelled with $^{99m}Tc$, where the radiolabelling reaction is carried out at basic pH is a most preferred embodiment of the present invention.

Radiolabelling as defined by the present invention is the chemical attachment of a radiometal, such as those described above. Suitable radiolabelled compounds of the invention have affinity for the ST receptor to enable diagnostic imaging of cancers of colorectal origin. Preferred radiolabelled compounds are thus cleanly labelled with the minimum production of by-products. An example of such a by-product is reduced hydrolysed technetium (RHT) in the case of $^{99m}Tc$ labelling. In a preferred embodiment of the invention, the peptide-chelate conjugate is labelled with $^{99m}Tc$ maintaining high RCP and low RHT levels. The results of various studies described in the Examples show that the preferred compounds of the present invention are stable to the labelling conditions and maintain their biological efficacy following radiolabelling.

The RHT levels are of particular importance in the case of $^{99m}Tc$-labelled conjugates of the present invention as one of the main biological targets is in the liver. RHT localises in the liver and thus if allowed to remain, will therefore increase background tissue activity, decrease target to background ratios and lead to an overall decrease in image quality. The amount of RHT is relatively low for all the preparations (Example 10). There is little difference between the labelling characteristics of CA1-$ST_{5-18}$ at conjugate levels of 12.5-100 μg, in terms of the rate of formation of species 2. However, there was an increase in RHT at reduced conjugate levels (Example 10).

Compared to the non-HPLC purified unfiltered preparation, both filtering and addition of methylene diphosphonate (MDP, which is known to reduce RHT levels) had a similar effect in reducing liver uptake (Example 24). Neither method reduced background tissue counts to the level seen with HPLC purified preparations but high quality images of liver metastases are still possible with non-HPLC purified preparations.

Radiolabelling of the peptide-chelate conjugate may be carried out in a suitable buffering system such as carbonate, borate, triethanolamine hydrochloride-NaOH, dimethylleucylglycine, tris(hydroxymethyl)aminomethane, 2-amino-2-methyl-1:3-propanediol-HCl, diethanolamine-HCl, Clark and Lubs solutions (Bower and Bates, J. Res. Nata. Bur. Stand. 55, 191 (1957), Glycine, Glycylglycine or TAPS®. The labelling reaction is preferably carried out at a basic pH, i.e., between pH 8.0 and pH 10, most preferably at a pH of around 8.5. Examples 5 and 6 describe conducting the radiolabelling reaction using either sodium hydroxide or borate buffer in order to maintain a suitable pH. A preferred method of the present invention is the use of a borate buffering system in the radiolabelling reaction.

The competition binding experiments carried out (as described in Example 15) investigated the relative potency of various ST peptide compounds. Ki values in the nM range suggest good binding of competing ligand. These data show firstly that variations outside the pharmacophore in the ST peptide make little difference to binding ($ST_{1-17}$ vs. $ST_{5-18}$, Ki 0.6 and 0.4 nM, respectively). The presence of CA3 on the ST peptide results in a small increase in Ki, i.e., a small resulting decrease in binding. The presence of CA1 has a greater effect on binding to reduce further the Ki value to 2.8 nM, almost a ten fold reduction in binding efficacy. Binding affinity in the nanomolar range is considered acceptably high and the resulting differences in reduced binding are not observed in vivo. The negative control demonstrated no binding (up to 500 μM).

The preferred compounds of the present invention demonstrated Ki values of less than 100 nM, indicating high affinity for the receptor (see Example 17). Of all the compounds tested, CA1-$ST_{5-18}$, CA3-$ST_{5-18}$ and CA1-$gly_3$-$Dglu_3$-$ST_{5-18}$ showed the greatest potency in this assay, with Ki values of 2.8 nM, 0.8 nM and 1.0 nM, respectively. The in vivo efficacy of these screened compounds is discussed below.

The data obtained in Example 15, and the high binding (Ki) of mock-labelled peptide (peptide subjected to the radiolabelling protocol in the absence of radiometal), supports the fact that the radiolabelled material is still bioactive.

In a third aspect, the invention also encompasses radiopharmaceutical preparations. By the term "radiopharmaceutical preparation" is meant a composition comprising the radiometal complex of the invention in a form suitable for human administration. For human administration a radiopharamceutical preparation must be sterile. It is preferably in an injectable form, e.g., for $^{99m}Tc$, reconstitution of the peptide-chelate conjugate with sterile pertechnetate in saline.

The radiopharmaceutical preparation of the present invention may also be provided in a unit dose form ready for human injection and could for example be supplied in a pre-filled sterile syringe. The syringe containing the unit dose would also be supplied within a syringe shield (to protect the operator from potential radioactive dose).

A fourth aspect of the present invention is the use of the radiopharmaceutical preparation of the invention for the imaging of cancer of colorectal origin. Imaging using the radiopharmaceutical preparation of the present invention may be carried out by means of PET or SPECT imaging, depending on the nature of the radiometal.

In a fifth aspect, the present invention provides kits for the production of the radiopharmaceutical preparation of the invention. Suitable kits are designed to give sterile radiopharmaceutical products suitable for human administration, e.g. via injection into the bloodstream. When the radiometal is $^{99m}Tc$, the kit comprises a vial containing the peptide-chelate conjugate for the metal together with a pharmaceutically acceptable reducing agent. Suitable such reducing agents are: sodium dithionite, sodium bisulphite, ascorbic acid, formaridine sulphinic acid, stannous ion, Fe(II) or Cu(I). The pharmaceutically acceptable reducing agent is preferably a stannous salt such as stannous chloride or stannous tartrate. Alternatively, the kit may comprise a metal complex which, upon addition of the radiometal, undergoes transmetallation (i.e., ligand exchange) giving the desired product. For $^{99m}Tc$, the kit is preferably lyophilised and is designed to be reconstituted with sterile $^{99m}Tc$-pertechnetate ($TcO_4^-$) from a $^{99m}Tc$ radioisotope generator to give a radiopharmaceutical solution suitable for human administration without further manipulation.

The peptide-chelate conjugate is preferably present in the kit in a form amenable to transport and storage over relatively long time-periods. Reconstitution with eluate from a $^{99m}Tc$ generator under the preferred radiolabelling conditions results in a $^{99m}Tc$-labelled peptide with specificity for the ST receptor. It is an important feature of the present invention that in such a kit, the radiolabelling reaction does not alter the affinity of the peptide for the ST receptor. $^{99m}Tc$-labelled peptides of the present invention have been shown to be stable for up to 4 hrs at room temperature and in the presence of activity levels of up to 1 GBq.

The above kits or pre-filled syringes may optionally contain further ingredients such as buffers; pharmaceutically acceptable solubilisers (e.g. cyclodextrins or surfactants such as Pluronic™, Tween™ or phospholipids); pharmaceutically acceptable stabilisers, radioprotectants or antioxidants (such as ascorbic acid, gentisic acid or para-aminobenzoic acid) or bulking agents for lyophilisation (such as sodium chloride or mannitol).

It is a feature of the invention that the metal complexes have maintained potency for the ST receptor as well as suitable pharmacokinetics. Data obtained in Example 16 indicate that positive control, $^{125}$I-ST$_{1-17}$ has the highest binding of 20% of added radioactive material. The negative control, CA3-T$_{5-18(Cys-Ala)}$, showed no specific binding (binding at NSB level, <1%). $^{99m}$Tc-labelled CA1-STs$_{5-18}$ shows reduced binding (6% of total added) compared to the positive control but is still significantly higher than that of the negative control. The compounds of the present invention also have optimal blood clearance, fast liver clearance and fast background tissue clearance. Liver clearance is a particularly significant feature of the present invention due to the high incidence of CRC metastases in that organ. Furthermore, the compounds of the present invention have been demonstrated to permit imaging of colorectal cancer metastases which are less than 1 cm in diameter. This is a feature which additionally permits distinction to be drawn between focal and diffuse metastases. It has not been previously possible to achieve these features in an agent directed towards the ST receptor. This is therefore a surprising development over the prior art.

Metal complexes of the present invention are cleared rapidly via the urine (>90% at 60 min p.i.). An additional feature of the present invention is low gastrointestinal uptake, which reduces the risk of unwanted side effects. Low uptake in background tissues such as liver, which may interfere with image quality, is an advantage of the metal complexes of the present invention. For CA1-ST$_{5-18}$ the liver uptake was 0.93% of the injected dose per gram at 2 hours p.i. (Example 17). CA1-ST$_{5-18}$ shows the greatest tumour to background tissue ratio, the greatest uptake (% ID/g) and relative retention of all the compounds assessed. This shows that of all the compounds examined, CA1-ST$_{5-18}$ showed the best pharmacokinetic qualities for a CRC imaging agent (Example 17).

The preferred mode of imaging of the present invention is SPECT imaging. It was demonstrated to be possible to image tumours of between 0.5-1 cm in diameter by SPECT imaging using the subcutaneous model (described in Example 17). The images acquired in Example 18 show that imaging is possible from 15 min p.i., and by 120 min p.i. only the tumour and kidneys are visible. The tumour size imaged was of the region expected in the target population. The images have been acquired in a planar mode, with a relatively low radioactive dose of 20 MBq/animal. Spatial resolution between organs is known to be better in humans such that the images obtained would be expected to be at least as good as seen in the animal models.

As shown in Examples 18, 19, 21 and 23, the preferred compounds of the invention display superior imaging properties not previously reported in the art. Specific in vivo tumour uptake has been demonstrated in two different animal models. These models are described in Examples 17 and 20. Imaging of both subcutaneous tumours and liver metastases was achieved at <2 hr p.i. in mice. It was possible to acquire images in mice from 15 minutes p.i. This will support the ideal clinical imaging window in humans of between 1-6 hours p.i.

Figure 4:
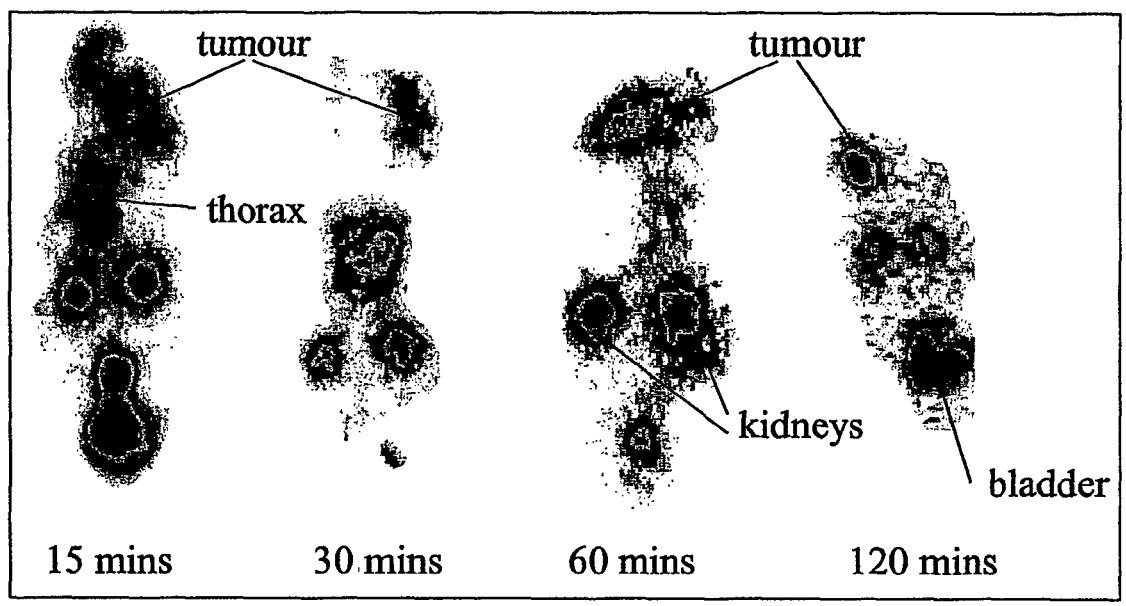
FIG. 4 shows SPECT images of mice bearing T84 tumours subcutaneously. The images are planar posterior static images with LEUHR collimator using HPLC purified $^{99m}$Tc-labelled CA1-$ST_{5-18}$ at 20 MBq per animal. Tumour to liver ratios were; 1.1 at 15 minutes, 2 at 60 minutes and 4 at 120 minutes. Image quality was comparable when crude preparations were used.
Figure 5:
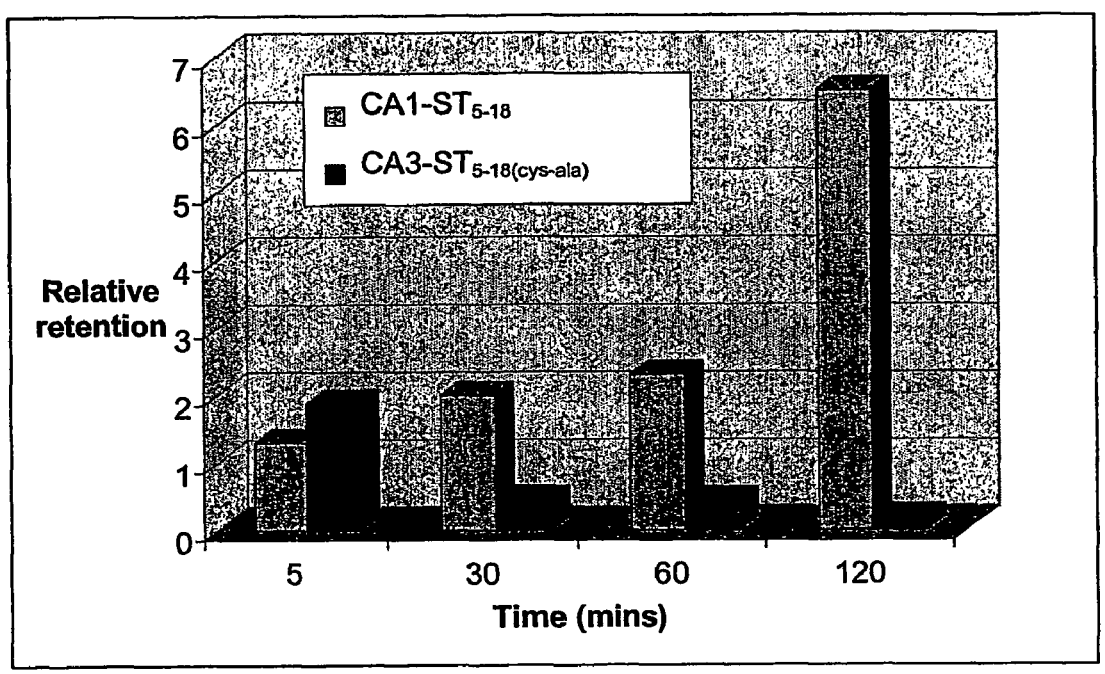
FIG. 5 shows the relative retention of CA1-$ST_{5-18}$ versus the negative control, CA1-$ST_{5-18(cys-ala)}$.
Figure 6:
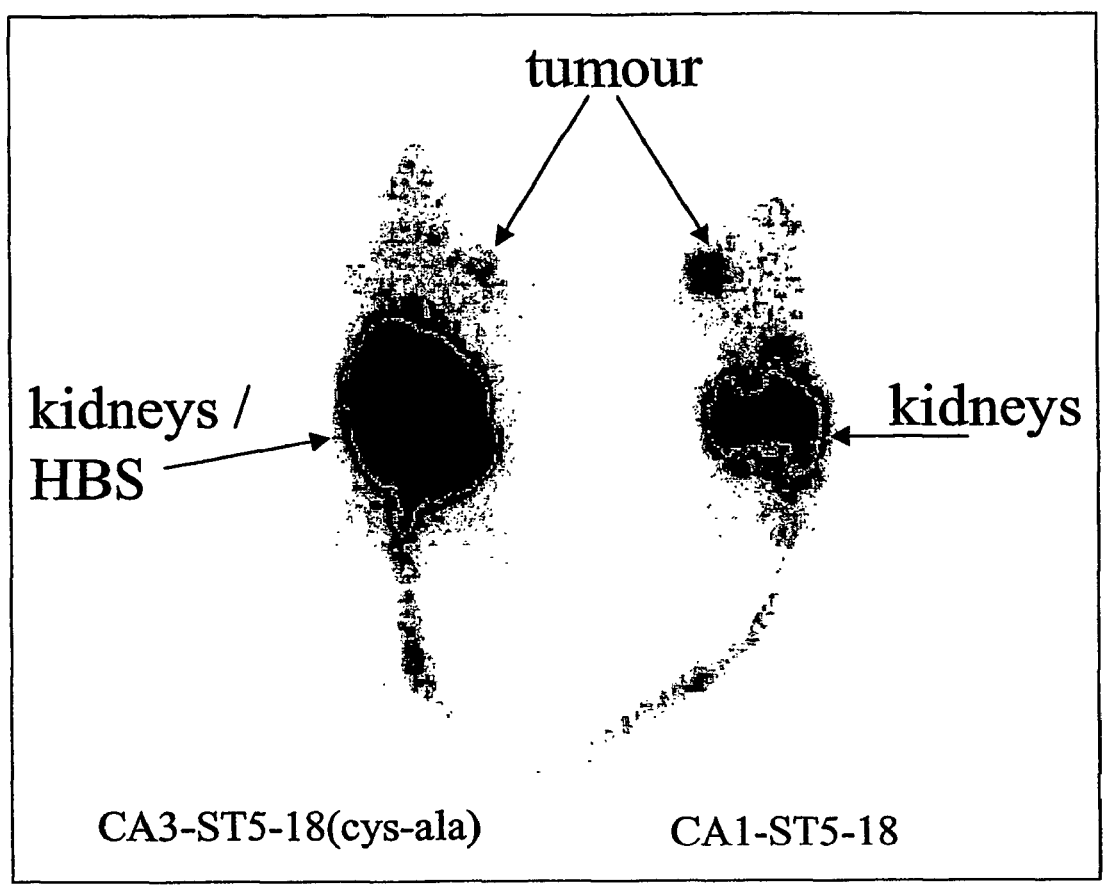
FIG. 6 shows a comparison of HPLC purified $^{99m}$Tc-labelled CA1-$ST_{5-18}$ and CA1-$ST_{5-18(cys-ala)}$ uptake in CD-1 nude mice bearing subcutaneous T84 tumours. Planar posterior static imaging with LEUHR collimator using HPLC purified CA1-$ST_{5-18}$ at 20 MBq per animal.

The images produced in Example 18 (FIG. 4) have consistently shown clear identification of tumours from 15 min p.i. with good ratios for tumour to muscle (not shown) and tumour to liver, which improves over time so that by 120 min p.i. only the tumour and kidneys are visible. The data obtained in Example 19 demonstrate good uptake for $^{99m}$Tc-labelled CA1-ST$_{5-18}$ and poor uptake for the negative control (FIG. 5). Planar posterior static images of the same animals acquired at 120-min p.i. show a similar pattern; good image of $^{99m}$Tc-labelled CA1-ST$_{5-18}$ and poor image of negative control (FIG. 6). In the image produced in Example 21 (FIG. 8), metastases are clearly visible, with a tumour:liver ratio of 1.5-3.0 based on ROI analysis. Images were acquired consistently and without major manipulation, with both of the formulations: HPLC purified and crude preparations.

Imaging experiments as described in Example 21 demonstrate specific retention of $^{99m}$Tc-labelled CA1-ST$_{5-18}$ into CRC tumours. These data support the specificity of $^{99m}$Tc-labelled CA1-ST$_{5-18}$ for ST-receptors, and highlight the importance of the conformational structure of ST peptides. When mice bearing sub-cutaneous Lewis lung tumours were injected with CA1-ST$_{5-18}$, as described in Example 22, significantly higher uptake of CA1-ST$_{5-18}$ into colorectal tumours than into those of non-colonic origin was demonstrated.

Literature studies indicate little variation in receptor expression between tumour samples, and the reported data (80-120 fmol/mg protein) compared well with the average expression found in this study. Although a large differential in receptor expression has been seen between the two human donors (Example 25)

In biodistribution studies on a range of xenograft tumours with different ST receptor expression, highest expression was shown in T84 cells but similar to the expression in human tumours (Example 25). The relative expression in a number of different cell lines was analysed and was found to be in the following order: T84>CaCO2>LS180>HT29>SW480. The data show comparatively higher retention of CA1-ST$_{5-18}$ in high ST receptor-expressing tumours, CaCO2 and T84, compared to the rest. Images of tumours expressing receptor density lower than that found in human tumours (LS180) was achieved, as a result CA1-ST$_{5-18}$ will be able to detect a wide range of human tumours.

Expected values from previous studies suggest little loss in expression with either origin of tumour or decrease in grade. Therefore, a population of patients with low ST receptor-expressing metastases is unlikely. More importantly, the expression of receptors in human CRC tumours lies directly in between that of two imageable CRC tumours, suggesting that expression of the receptor in Human tumours is sufficient for imaging with $^{99m}$Tc-labelled CA1-ST$_{5-18}$. Low retention in tumours was observed with the negative control, CA3-ST$_{5-18(cys-ala)}$. The data also show that despite very low receptor density there is still specific retention of $^{99m}$Tc-labelled CA1-ST$_{5-18}$ in those tumours. The tumour uptake in tumours from T84 and LS180 cells, grown subcutaneously or in the liver of immunocompromised animals, is sufficient for imaging, as demonstrated in both the subcutaneous model and in the liver metastases model. By doing so it has been shown that it is possible to image small tumours in the region of expression levels of ST receptor found in human tumours.

The compounds of the present invention satisfy all major requirements identified for an improved CRC imaging agent, in particular successfully imaging tumours in an animal model thought to represent the more challenging aspects of the clinical disease. Exceptional efficacy has been demonstrated in the critical efficacy model of liver metastases. The preferred embodiments allow imaging of tumours that represent the range of receptor densities found in human liver metastases from CRC. The efficacy is maintained in the presence of excess peptide, at levels expected in a potential clinical formulation hanging studies have shown that preferred compounds are likely to be more sensitive and specific than X-ray CT. The compounds of the present invention could thus be used in the initial diagnosis of disease, and more importantly in the appropriate staging or determination of the extent of the disease, measuring response to therapy and in the follow up of patients treated for primary CRC.

The compounds of the present invention are therefore superior to any other reported CRC imaging compound. They are retained specifically in tumours of CRC origin. Imaging potential was demonstrated in a clinically acceptable time frame in a desired target tumour size. Surprising uptake, retention, pharmacokinetics, and efficacy have been demonstrated in view of reported instability of the vector at basic pH.

EXAMPLES

Example 1

Peptide-Chelate Conjugates

The compounds used are given in Table I. Conjugates were prepared as described in Example 2 as 100 µg aliquots in plastic vials, and stored at −18° C. The conjugates were allowed to warm to ambient temperature before use.

TABLE I

Compounds of the invention

CA3-ST$_{5-18}$

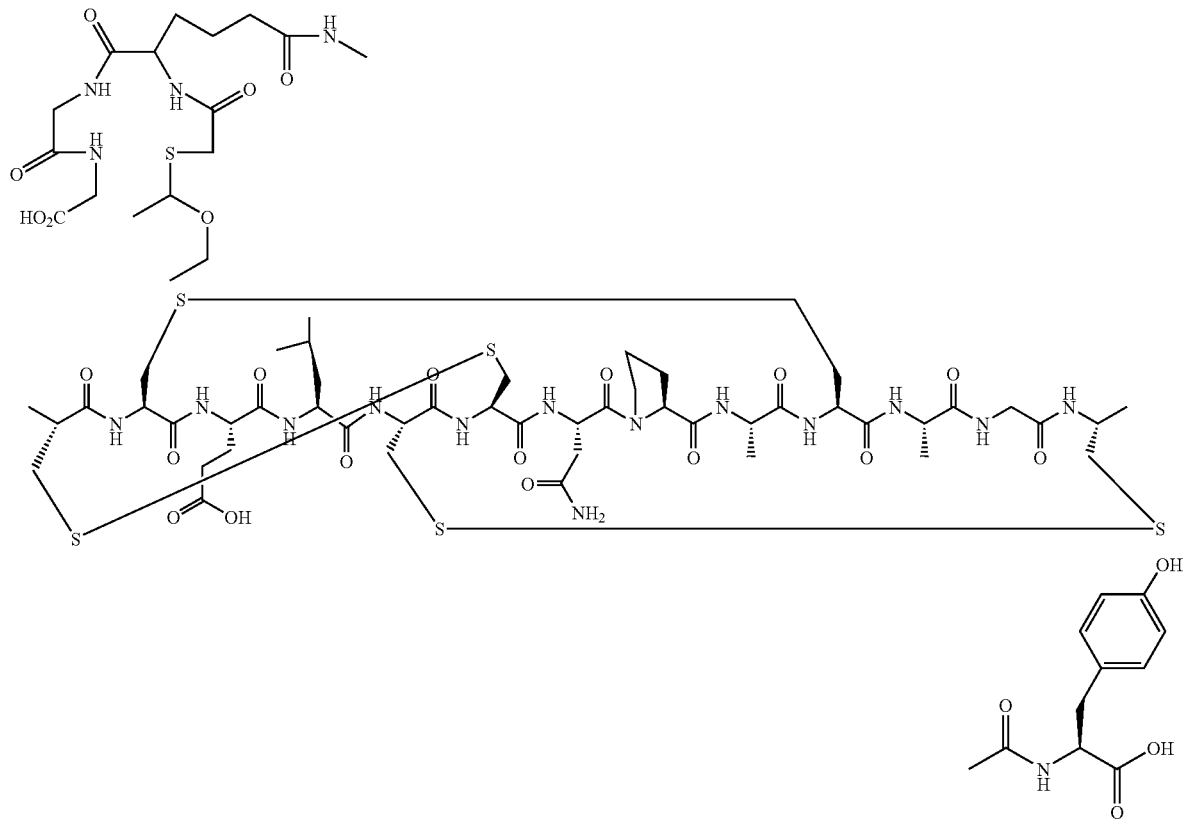

CA3-ST$_{5-18\ (cys-ala)}$

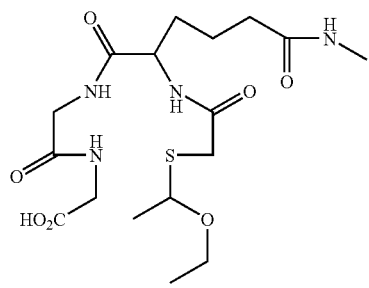

TABLE I-continued
Compounds of the invention
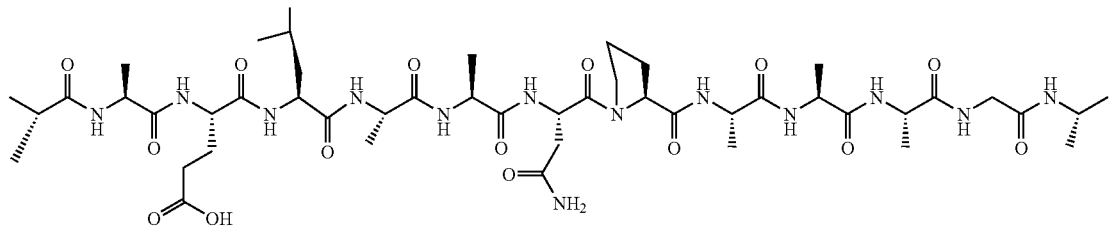
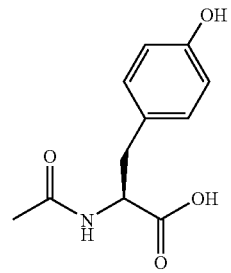
CA1-ST{5-18}
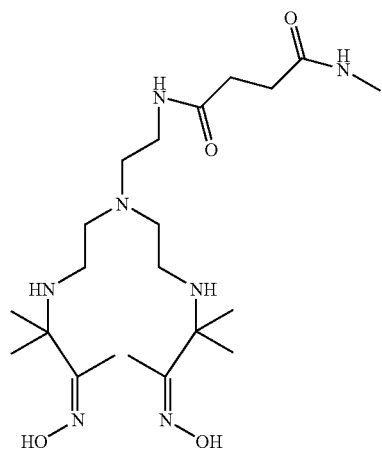
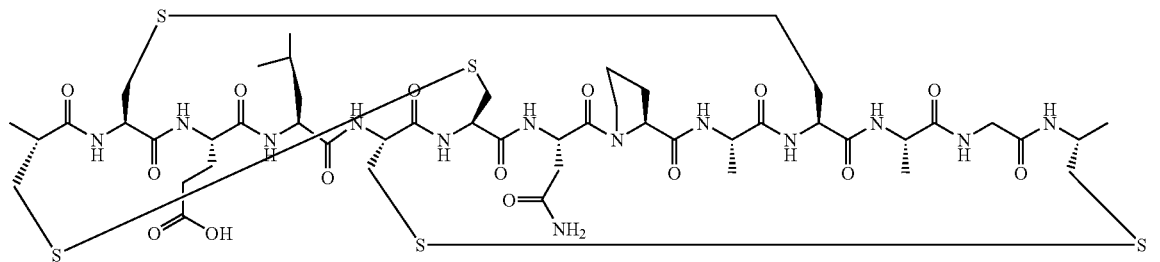
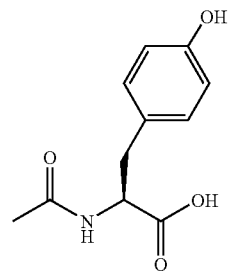
CA2-(Gly)2-Glu-(Lys)3-ST{5-18}

TABLE I-continued
Compounds of the invention
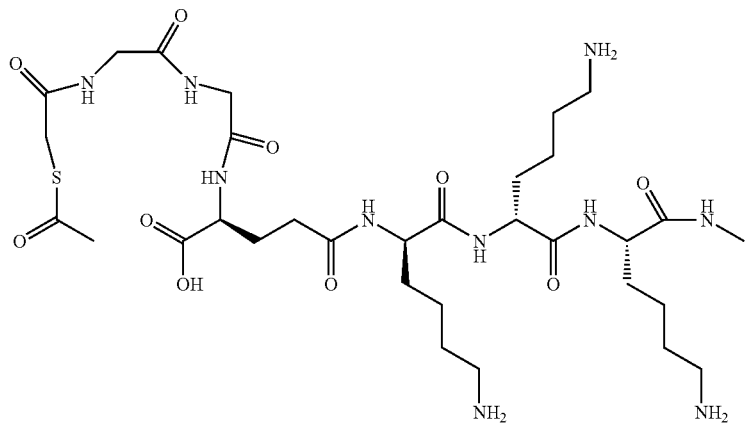
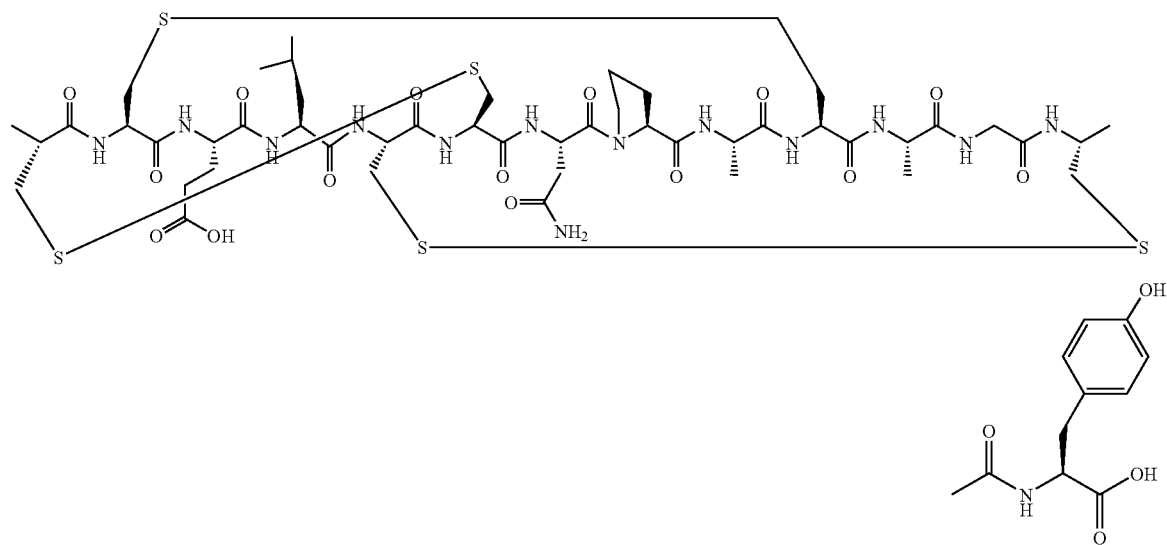
CA₂-(Gly)₂-Glu-Lys-Glu-Lys-ST₅₋₁₈
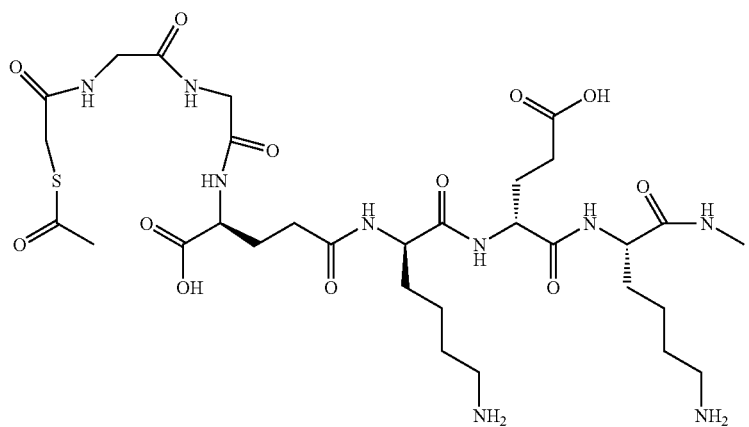

TABLE I-continued
Compounds of the invention
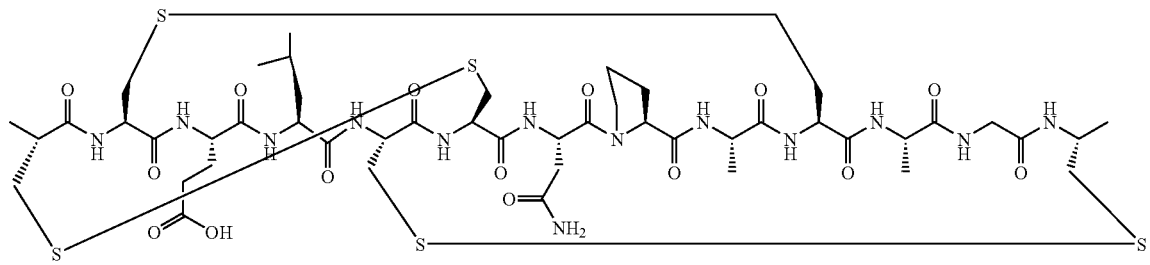
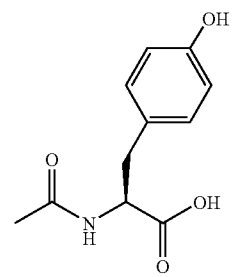
ST$_{5-17}$ C terminus amide
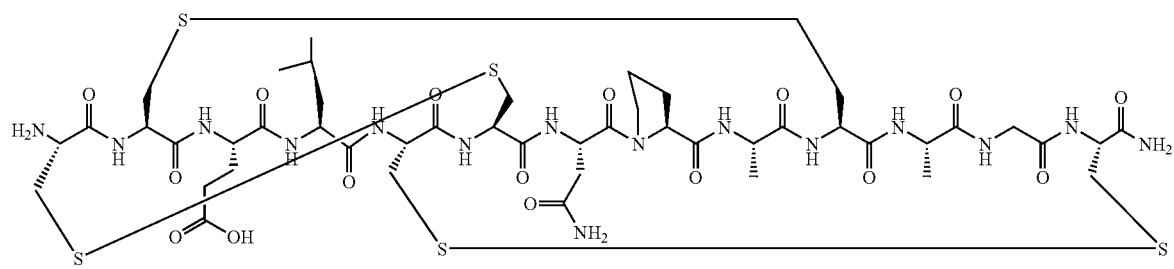
CA2-(Phe)$_2$-(CH$_2$)$_5$-ST$_{5-18}$
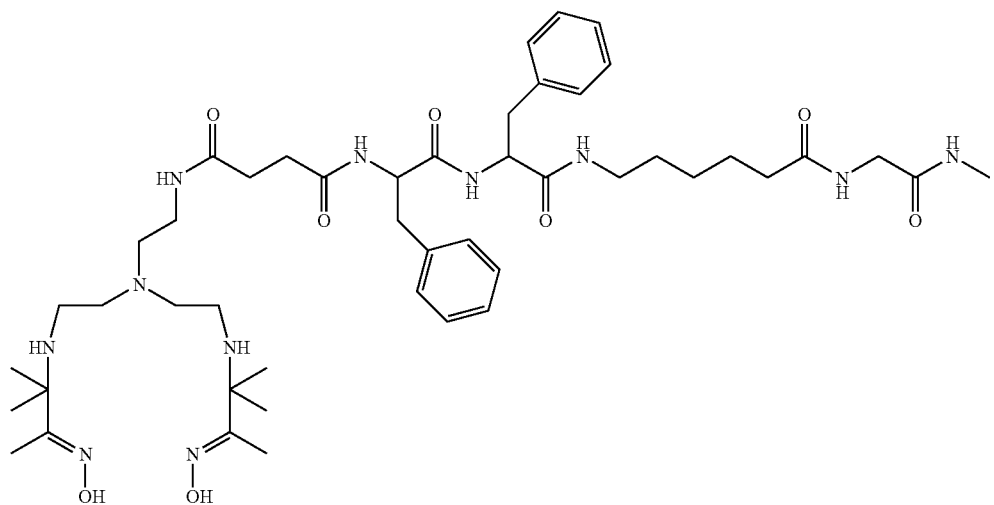

TABLE I-continued

Compounds of the invention

CA1-(Glu)₆-ST₅₋₁₈

TABLE I-continued

Compounds of the invention

CA1-(Lys)₆-Gly-ST₅₋₁₈

TABLE I-continued

Compounds of the invention

CA1-(Gly)$_3$-(D-Glu)$_3$-ST$_{5-18}$

CA1-(Gly)$_3$-(aminocaproic acid)$_2$-ST$_{5-18}$

TABLE I-continued

Compounds of the invention

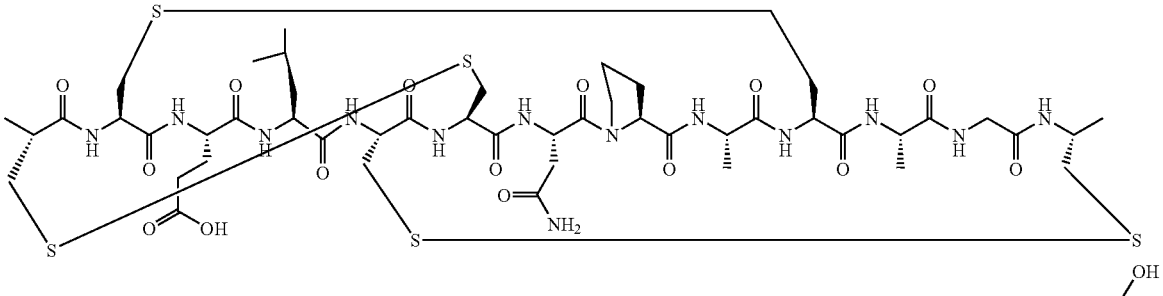

Example 2

Synthesis of CA1-ST$_{5-18}$ 2.1 Solid-Phase Synthesis

The solid-phase assembly of the peptide sequence was performed on the support Fmoc-Tyr(tBu)-SASRIN (10 g polymer; 0.6 mmol/g loading) using an Advanced Chemtech 90 automated peptide synthesiser. The amino acids were all of the L-configuration with the α-amino function blocked with the 9-Fluorenylmethoxycarbonyl (Fmoc) protecting group.

The reactive side-chain functional groups were bearing the following protecting groups:
Trityl (Trt)—for cysteines 6 and 14 and asparagine,
Acetamidomethyl (Acm)—for cysteines 5 and 10,
4-Methoxybenzyl (Mob)—for cysteines 9 and 17,
tert-Butyl ester—for glutamic acid
tert-Butyl ether—for tyrosine 2.2 Coupling and Deprotection Reactions Double coupling cycles were carried out using a 5-fold excess of activated Fmoc-amino acid derivatives dissolved in N-methylpyrrolidone (NMP). The first coupling was carried out with Fmoc amino acid/DIC/HOBt activation, and the second coupling with Fmoc amino acid/HBTU/HOBt/DIEA activation.

Excess reagents were removed from the polymer by washing three times with NMP, three times with methanol and three times with NMP before removal of the Fmoc group in 20% piperidine/NMP (5 minute and 20 minute cycles performed). Once assembled the peptide resin was washed three times with NMP, three times with DCM and three times with methanol before drying overnight in a vacuum oven at room temperature. Weight of final resin 20.76 g (yield 84.2%).

2.3 Cleavage of Partially Protected Peptide from the Solid Support

To the dry peptide resin in the nitrogen bubbler was added TFA (25 ml) containing 5% TIS and 5% water and the mixture bubbled under nitrogen for 30 minutes. The peptide solution was then drained into toluene (200 ml) and evaporated in vacuo at RT. Cold diethyl ether was added to the oily residue in order to precipitate out the product as a solid. Following trituration with diethyl ether and drying, 600 mg of the crude dithiol peptide was obtained. The HPLC purity of the crude product was shown to be around 70% with several side-products identified due to modifications during the TFA cleavage step. The most significant impurity (10-15%) was caused by the cleavage of one of the CA1 oxime side arms.

2.4 Cyclisation 1: oxidation of the crude dithiol peptide: 6,14 disulphide

Crude dithiol peptide from 2.3 above (0.132 mmol, 300 mg) was dissolved portionwise in 600 mL of 0.1M NH$_4$HCO$_3$ (pH 8) in water/acetonitrile (80:20) containing potassium ferricyanate (0.3 mmol, 100 mg). The reaction was left stirring under nitrogen for 16 hours then HPLC analysis was used to confirm complete conversion of starting dithiol to oxidised product. The peptide solution was then acidified to pH 2 with TFA, filtered through a 0.45 micron filter (Millipore) then pumped directly onto the preparative HPLC column and gradient elution initiated. Fractions of >80% purity were combined and freeze-dried yielding 140 mg of the desired product.

2.5 Cyclisation 2: Acm Group Deprotection and Cyclisation 6,14: 5,10

The mono-disulphide product from 2.4 above (0.14 g, 0.062 mmol) was dissolved in 150 ml of acetic acid/DMSO (1:1) containing 0.1 mL anisole and iodine (0.1 g, 0.39 mmol) added. The reaction mixture was stirred in the dark for 30 minutes before dilution to a total volume of 450 ml with distilled water. The peptide solution was then extracted twice with diethyl ether in a separating funnel and the aqueous phase analysed by HPLC.

HPLC analysis revealed the presence of two new products present in a 4:1 ratio. Both products had the desired molecular weight as evidenced by MS analysis and corresponded to two conformational isomers. The aqueous layer was once again filtered through a 0.45 micron filter (Millipore) before pumping directly onto the preparative BPLC column and gradient elution initiated. Fractions of >80% purity were combined and freeze-dried yielding 40 mg of the desired product.

2.6 Cyclisation 3: Mob Group Deprotection and Cyclisation

To the bis-disulphide product from 2.5 above (40 mg, 0.019 mmol) was added a solution of 10% DMSO/TFA (50 ml) containing 0.1 ml of anisole and the mixture gently shaken (20 min.). The TFA was evaporated in vacuo at room temperature and the product precipitated by the addition of diethyl ether. Following trituration with diethyl ether 25 mg of the fully folded product was recovered. Preparative HPLC of crude product and freeze-drying yielded 16 mg of the desired product (purity >98%). MS analysis by LCQ; found (M+H)+=1873, expected (M+H)+=1873.

2.7: Salt Exchange

The pure TFA salt from above was dissolved in water containing 0.1% ammonium acetate. Gradient elution on a C18 reverse phase column using a 10 to 60% B gradient over 40 minutes where buffer A=0.1% ammonium acetate/$H_2O$; B=0.1% ammonium acetate in 80% acetonitrile/$H_2O$) was performed. The acetate salt (15 mg) was recovered following freeze-drying.

Example 3

Synthesis of Chelating Agent 1 (CA1)

To a solution of tris-(2-aminoethyl) amine (Aldrich; 2 ml, 13 mmol) in acetonitrile (20 ml) was added sodium bicarbonate (2.2 g, 26 mmol). A solution of 3-chloro-3-methyl-2-nitrosobutane (1.8 g, 13 mmol) in dry acetonitrile (10 ml) was added slowly at 0° C. The reaction mixture was left to stir at room temperature for 4 hours, and then filtered. The filtrant was washed with acetonitrile and the filtrate evaporated. The crude product was dissolved in acetonitrile and purified by HPLC (Hamilton PRP-1; A: 2% aqueous $NH_3$, B: MeCN; 0-100% B in 20 min; 3 ml/min) to afford CA1. Yield: 0.88 g, 19%.

Example 4

Conjugation of Peptide to Chelating Agent 4.1 Coupling of Succinic Acid Linker

An aliquot (1 g, ca 0.3 mmol) of the peptide resin from Example 2 was transferred to a nitrogen bubbler where a further set of washes in DMF (3×15 ml) were carried out. A solution containing 1 mmol of succinic anhydride dissolved in DMF (20 ml) was then added and the mixture bubbled under nitrogen for 30 minutes. The polymer was washed with 5×15 ml quantities of DMF and a resin sample taken for analysis by Kaiser Test to confirm the absence of free amino groups.

4.2 Coupling of Chelating Agent 1(CA1)

The resin bound acid functionality was then pre-activated in situ by the addition of a solution in DMF (15 ml) containing PyAOP (0.52 g, 1 mmol), HOAt (0.14 g, 1 mmol) and NMM (0.2 ml, 2 mmol). On-resin activation was carried out for 10 minutes followed by addition of a solution in DMF (10 ml) of CA1 (0.4 g, 1.1 mmol). The mixture was bubbled for 3 hours then excess reagents removed by filtration followed by washing with DMF (5×15 ml), DCM (3×15 ml) and ether (3×15 ml). The peptide-resin was then dried in a stream of nitrogen.

Example 5

Radiolabelling: Sodium Hydroxide Method

An aliquot of conjugate (100 µg) was dissolved in nitrogen-purged saline (900 µl) and added to a silanised P6 vial using silanised pipette tips. The pH of the solution was adjusted to pH 8.5 with 0.01M sodium hydroxide solution and the vial capped. To the solution was added $Na^{99m}TcO_4$ (1 ml, 1 GBq/ml) from a freshly eluted generator (eluate less than 2 hours old). The pH of the solution was again adjusted to pH 8.5 with 0.01M sodium hydroxide solution. Freshly prepared nitrogen-purged $SnCl_2$ solution (0.1 ml, 10 mg/100 ml saline) was then added to the solution. The pH of the solution was again adjusted to pH 8.5 with 0.01M sodium hydroxide solution. The vial was shaken after each addition to ensure mixing. The preparation was left to stand at room temperature.

Example 6

Radiolabelling: Borate Buffer Method 12.5 mM borate buffer (1 ml) was added to an aliquot of conjugate and sonicated for 30 seconds. The resulting solution was added to a silanised P6 vial, using silanised pipette tips, and the vial capped. To the solution was added $Na^{99m}TcO_4$ (1 ml, 1 GBq/ml) from a freshly eluted generator (eluate less than 2 hours old). Freshly prepared nitrogen-purged $SnCl_2$ solution (0.1 ml, 10 mg/100 ml saline) was then added to the solution. The vial was shaken after each addition to ensure mixing.

Example 7

Labelling Analysis

Investigation of the labelling characteristics of the CA1 conjugates was performed by labelling CA1-$ST_{5-18}$ using the sodium hydroxide method outlined in Example 5. Simultaneous HPLC and ITLC analysis was performed at approximately 15, 60 and 120 minutes post reconstitution. In addition, preparative HPLC was performed to obtain pure samples of the two $^{99m}Tc$ species. ITLC analysis was performed on each purified sample to confirm agreement between the two analytical techniques. Further studies were performed on alternative CA1 conjugates to confirm the observed labelling characteristics.

The results of the initial investigation of the labelling characteristics showed a single major $^{99m}Tc$ species at early time points, converting almost completely to a second species over a number of hours. Good agreement between ITLC and HPLC analysis was observed. Two $^{99m}Tc$-conjugate species were resolved by both HPLC and ITLC and the relative quantities of each species correlated well. For further confirmation, preparative HPLC was performed to obtain pure samples of the two species.

Example 8

Effect of pH on Radiolabelling

The effect of pH on the labelling characteristics was investigated by comparing the labelling of CA1-$ST_{5-18}$ (100 µg), using the borate buffer method outlined in Example 6, at pH 8.1, 8.5 and 9.0. ITLC analysis was performed at 15, 30, 60, 90, 120 and 180 minutes post-reconstitution. A relatively narrow pH range was studied due to the known instability of the $ST_{5-18}$ vector to high pH, caused by the presence of three disulphide bridges.

The results of the comparison of the labelling of CA1-$ST_{5-18}$ at pH 8.1, 8.5 and 9.0 are shown (FIG. 1). The results are expressed as % species 2 formed, as seen by ITLC (Gelman ITLC/SG paper, 70:30 saline: acetonitrile eluent) analysis.

Example 9

Effect of Temperature on Radiolabelling

The effect of temperature on the labelling characteristics was investigated by comparing the labelling of CA1-$ST_{5-18}$ (100 µg), using the borate buffer (pH 9.0) method outlined above, followed by heating at 40, 60 and 75° C. Each preparation was allowed to stand at room temperature for 10 minutes post reconstitution then heated for 20 minutes. ITLC analysis was performed prior to heating (10 minutes post reconstitution), 10 minutes post heating (40 minutes post reconstitution) and 60 minutes post heating (100 minutes post reconstitution).

Figure 2:
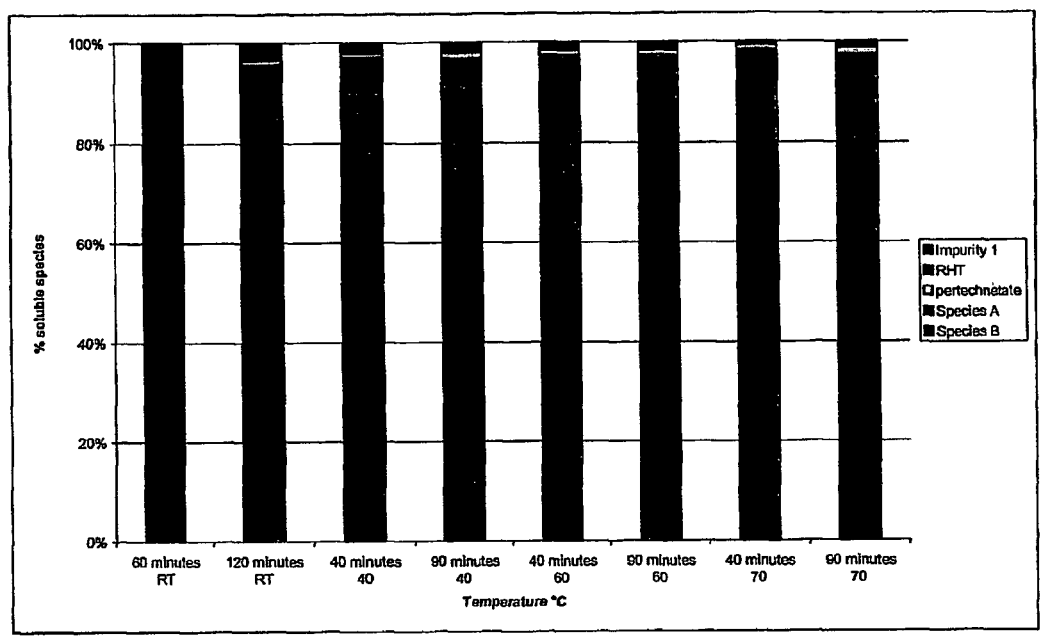
FIG. 2 shows the effect of varying the temperature of the radiolabelling reaction on the formation of Species 2 (CA-$ST_{5-18}$). The temperatures evaluated were 40° C., 60° C. and 70° C.

The results of the comparison of the labelling of CA1-$ST_{5-18}$ at 40, 60 and 70° C. are shown (FIG. 2). The results are again expressed as % Peak 2 formed, as measured by ITLC (Gelman ITLC/SG paper, 70:30 saline: acetonitrile eluent) analysis.

Example 10

Effect of Conjugate Level on Radiolabelling

The effect of conjugate level on the labelling characteristics was investigated by comparing the labelling of various amounts of CA1-$ST_{5-18}$ (12.5, 25, 50 and 100 µg) using the borate buffer (pH 9.0) method outlined above. ITLC analysis was performed at 15, 30, 60, 90, 120 and 180 minutes post reconstitution.

Figure 3:
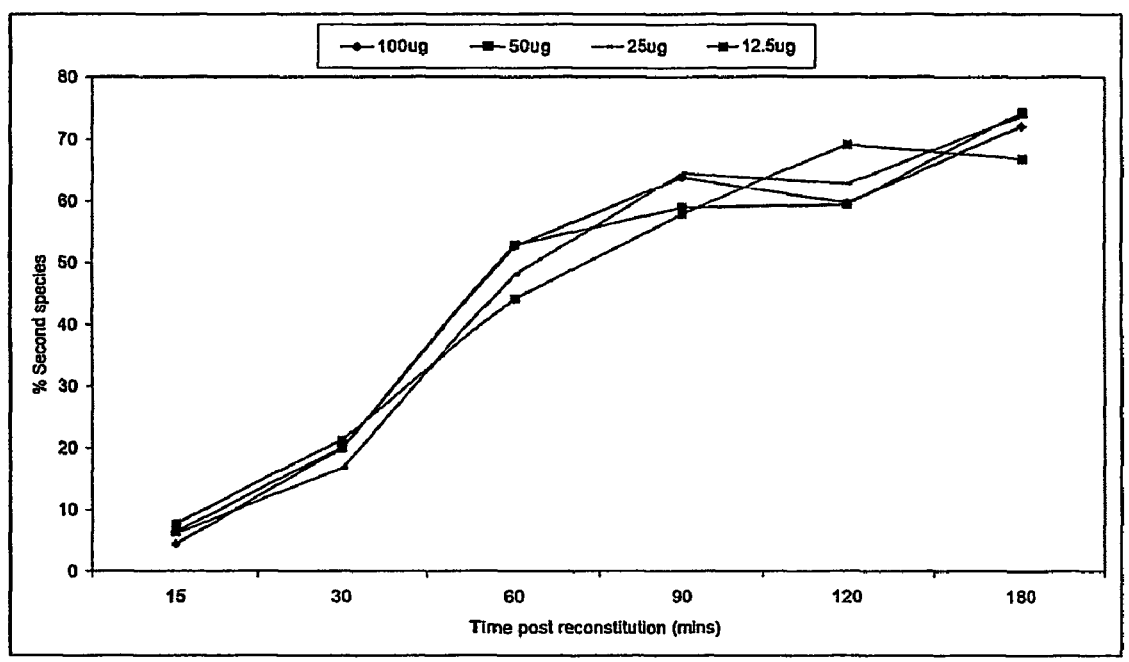
FIG. 3 shows the effect of compound mass on the percent formation of Species 2 (CA-$ST_{5-18}$), tested at 12.5 µg, 25 µg, 50 µg and 100 µg compound.

The results of the labelling CA1-$ST_{5-18}$ at varying levels (12.5, 25, 50 and 100 µg, equivalent to $6.6 \times 10^{-9}$, $1.3 \times 10^{-8}$, $2.7 \times 10^{-8}$ and $5.3 \times 10^{-8}$ moles) are shown (FIG. 3). The results are expressed as the percentage of species 2 formed, as seen by ITLC (Gelman ITLC/SG paper, 70:30 saline: acetonitrile eluent) analysis. RHT data has been shown (Table II).

TABLE II

| | RHT levels in radiolabelled preparations. | | | |
|---|---|---|---|---|
| | 100 µg | 50 µg | 25 µg | 12.5 µg |
| RHT (%) | 0.6 | 1.5 | 1.9 | 2.7 |

Example 11

Stability of Conjugate to Labelling Conditions

To establish the stability of the starting material to the labelling conditions, an inactive, "blank" labelling experiment was performed. A "blank" labelling involved the substitution of saline for $Na^{99m}TcO_4$. CA1-$ST_{5-18}$ (100 µg) was subjected to the borate buffer labelling method (pH 9.0, 60° C., 20 minutes). The starting material was then HPLC purified and a competition binding assay performed to determine whether there was any loss of affinity for the receptor compared with before the labelling procedure. HPLC analysis was performed to detect any degradation of the compound.

No degradation of the compound was observed by HPLC and potency (measured by competition binding assay) did not significantly alter.

Example 12

Competition between CA1-benzamide and $ST_{5-18}$

To investigate co-ordination of $^{99m}Tc$ to the peptide conjugate, a competition study was performed. Firstly, CA1-benzamide (which was chosen to mimic the CA1 portion of CA1-$ST_{5-18}$) and $ST_{5-18}$ were labelled independently using the borate buffer method (pH9.0, 60° C. for 20 minutes) and characterised by HPLC and ITLC. For the competition study, equimolar quantities of CA1-benzamide (31 µg, $6.92 \times 10^{-8}$) and $ST_{5-18}$ (100 µg, $6.92 \times 10^{-8}$) were labelled together in the same pot using the borate buffer method. ITLC and HPLC analyses, as outlined in Examples 13 and 14, determined where the technetium had coordinated.

Example 13

ITLC

Gelman ITLC/SG paper eluted with saline

Gelman ITLC/SG paper eluted with methylethyl ketone (MEK, 2-butanone)

Gelman ITLC/SG paper eluted with a 70:30 v/v mixture of saline and acetonitrile

Whatman No. 1 (W1) paper eluted with a 50:50 v/v mixture of water and acetonitrile

Example 14

HPLC

All analysis was carried out using Gilson hardware and Unipoint software.

Column: Phenomenex Luna C-18, 4.6×250 mm, 5 µm

Eluent A:0.1% acetic acid (pH raised to pH 5.0 with ammonia) in 90% water/10% acetonitrile Eluent B:0.1% acetic acid (pH raised to pH 5.0 with ammonia) in 10% water/90% acetonitrile Flow:1 ml/min UV Detector:)λ=230 mn Similar gradients were used for the different conjugates. A typical gradient was:

$T_0$:0% B $T_5$:15% B $T_{20}$:15% B $T_{21}$:0% B $T_{30}$:0% B

Example 15

Competition Binding Assay

Compounds were assessed for their potency by radioligand binding assay to determine inhibition constant (Ki) as a measure of potency of binding. Methods are described elsewhere, but briefly, [$^{125}$I]ST$_{1-17}$ was competed with cold ST compounds (0.0001-50 μM) in 96 well plates containing ca. 1 μg rat intestinal membrane and incubated 1 hr, 37° C. Samples were filtered (GF/B filters, Whatman) to retrieve bound radiolabelled peptide and counted to determine % Bound/Free.

Potency of compounds was determined by inhibition constant (Ki) for their ability to compete with radioligand, [$^{125}$I]ST$_{1-17}$. Potencies of screened compounds are shown in Table III.

TABLE III

Ki assay data for CRC compounds. Ki values shown are means of triplicate values of assay wells. Non-specific binding accounts for less than 0.1% in all cases and total binding (no competing peptide) is no greater than 20%.

| Compound | Mean Ki value (nM) | Comments |
|---|---|---|
| ST$_{1-17}$ | 0.6 | ST peptide |
| ST$_{5-18}$ | 0.4 | Selected Core Vector |
| CA3-ST$_{5-18}$ | 0.8 | Labelled |
| CA3-ST$_{5-18(cyc-ala)}$ | none | Negative Control |
| CA1-ST$_{5-18}$ | 2.8 | Unlabelled |
| CA-ST$_{5-18}$ | 3.5 | Mock-labelled |

Example 16

Radioactive Binding Assay

To determine whether radiolabelling affected the binding of the compound, labelled compounds were tested for their ability to bind the receptor. Briefly HPLC purified radiolabelled compounds (ca. 0.05 nM) were incubated with 6 μg/150 μl final volume of rat intestinal membrane (one hour), in the presence and absence of competing peptide (50 μM ST$_{5-18}$). Samples were filtered (GF/B filters, What-man) to retrieve bound radiolabelled peptide and counted to determine % Bound/Free. Non-specific binding accounted for less than 1% in all cases.

In order to ensure that potency was maintained post-labelling, an assay measuring binding of labelled compounds was developed.

Example 17

Biodistribution in a Subcutaneous Tumour Model

The sub-cutaneous model was used as an appropriate initial in vivo screen. Briefly, mice (female nude CD-1, ca. 20 g; Charles River) were injected sub-cutaneously into the neck with T84 human colon carcinoma cells (0.1 ml, 1×10$^8$ cells/ml in medium) through a 23-gauge needle and allowed to develop tumours over 6-8 weeks.

At least three animals per test point were studied. Results are expressed as % injected dose per gram (% ID/g) of tissue. Due to the fast clearance of $^{99m}$Tc-labelled CA1-ST$_{5-18}$ (greater than 90% excreted via urine 60 mins p.i.) tumour uptake is also expressed as relative retention (RR).

Compounds were screened for their uptake into sub-cutaneous T84 tumours in the mouse (Table IV). This model allows assessment of the imageability of CA1-ST$_{5-18}$ by allowing comparison between tumour and background tissue uptake.

TABLE IV

Screening data for compounds of the invention.

| Screen | CA3-ST$_{5-18(cys-ala)}$ | CA3-ST$_{5-18}$ | CA1-ST$_{5-18}$ | CA1-lys$_6$-gly-ST$_{5-18}$ | CA1-gly$_3$-Dglu$_3$-ST$_{5-18}$ |
|---|---|---|---|---|---|
| Ki value (nM) | none | 0.8 | 2.8 | 72 | 1 |
| HBS (% id at 2 hours p.i.) | 26 | 5 | 1.0 | 1.48 | 0.71 |
| Urinary (% id at 2 hours p.i.) | 32 | 90 | >90 | 76 | 63 |
| Liver (% id at 2 hours p.i.) | 0.93 | 0.5 | 0.1 | 4.9 | 0.46 |
| Tumour uptake & ratios | | | | | |
| % id/g at 2 hours p.i. | 0.21 | 0.8 | 0.94 | 1.0 | 0.26 |
| RC at 2 hours p.i. | 0.1 | 0.24 | 0.32 | 0.3 | 0.08 |
| RR at 2 hours p.i. | 0.17 | 2.5 | 6.4 | 1.6 | 1.9 |
| Tumour/liver | 0.08 | 2 | 12.4 | 0.23 | 0.63 |
| Retention over 2 hours | 8 | 30 | 20 | 34 | 5.5 |

Example 18

Imaging in the Subcutaneous Tumour Model

Tumours were grown as in Example 17. Animals were monitored for tumour growth for 8 to 10 weeks, until tumours were 0.5-1 cm in size. After this time, animals were injected with test article (0.1 ml, 20 MBq/ml or 200 MBq/ml) as an intravenous bolus via the tail vein. At various times p.i. animals were euthanased and whole body planar images acquired between 5 minutes and 24 hours p.i. using a gamma camera (Park Medical Isocam-1). Image acquisition times were typically 15-30 min or 150-250K counts (whole body, LEUHR collimator).

Example 19

Uptake of $^{99m}$Tc-labelled CA1-ST$_{5-18}$ and CA3-ST$_{5-18(cys-ala)}$ (Negative Control) into CRC Tumours CA3-ST$_{5-18(cys-ala)}$ has the same peptide sequence as $^{99m}$Tc-labelled CA1-ST$_{5-18}$, except all cysteines have been replaced by alanine amino acids, removing the three disulphide bridges required for binding. CA3-ST$_{5-18(cys-ala)}$ also contains the CA3 as opposed to CA1 and so was labelled using a suitable protocol for this chelate. To examine the uptake and retention of CA3-ST$_{5-18(cys-ala)}$ and $^{99m}$Tc-labelled CA1-ST$_{5-18}$, CD-1 nude mice bearing sub-cutaneous T84 tumours were injected, euthanased and dissected at various times p.i. The data is presented in FIGS. 5 and 6.

Example 20

Biodistribution in Liver Metastases Model

The liver metastases model was used in both mice and rats. As for the subcutaneous tumour model except in establishing tumours, cells were injected via the spleen and allowed to transfer to the liver via the circulation. Two minutes after injection of cells, a splenectomy was performed. Animals were allowed to generate tumours over 6-8 weeks.

Figure 7:
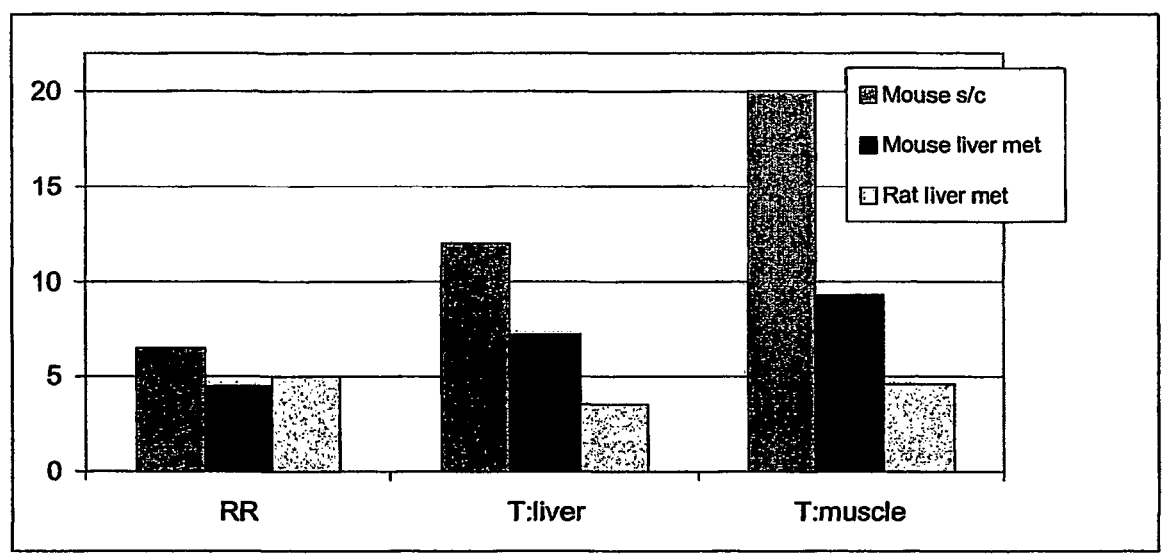
FIG. 7 shows the biodistribution of purified CA1-$ST_{5-18}$ at 2 MBq per animal in RNU/mu nude rats and mice bearing T84 liver tumours. The data is expressed in as relative retention (RR) and ratios of tumour to liver and tumour to muscle.

Animals were monitored for tumour growth for 8 to 10 weeks, until tumours were 0.5-1 cm in size. After this time, animals were injected with test article (0.1 ml, 20 MBq/ml or 200 MBq/ml) as an intravenous bolus via the tail vein. At various times p.i. animals were euthanased. Muscle, kidneys, urine, lung, liver, stomach, small intestine, large intestine, thyroid and tumour were dissected and a blood sample taken. Dissected tissues, blood samples and standards were weighed and counted (Wallac Wizard). At least three animals per test point were studied. Results are expressed as % ID/g of tissue. Due to the fast clearance of $^{99m}$Tc-labelled CA1-ST$_{5-18}$ (greater than 90% excreted via urine 60 mins p.i.) tumour uptake is also expressed as RR (FIG. 7).

Example 21

Imaging in Liver Metastases Model

Figure 8:
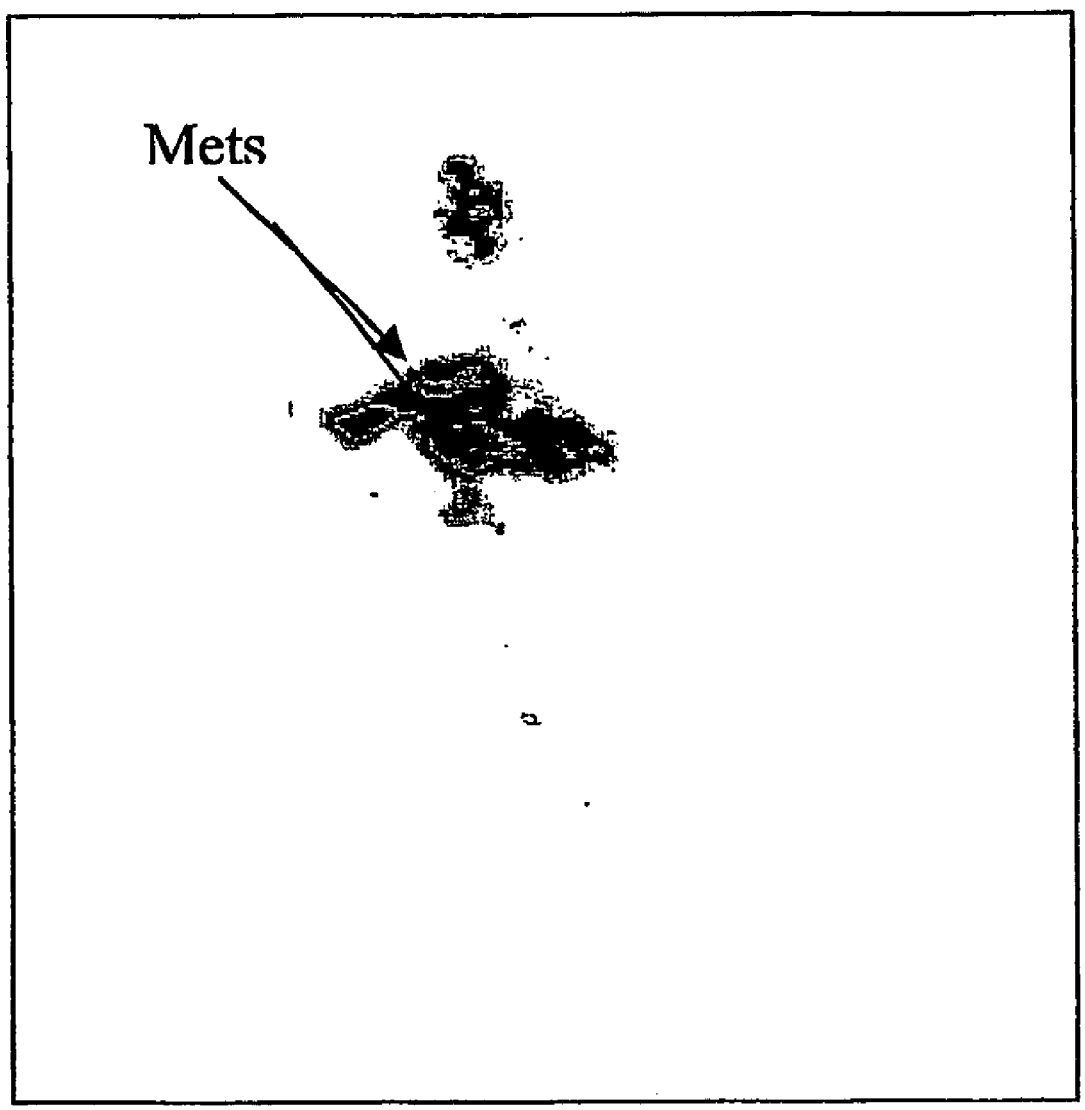
FIG. 8 shows an image of an RNU/rnu nude rat bearing T84 liver tumours. It is a planar posterior static image at 120 minutes post-injection (p.i.) using HPLC purified CA1-ST$_{5-18}$ at 20 MBq with LEUHR collimator. The image is a whole body image with background counts removed and kidneys masked. Image tumour:liver ratio was typically 2.5.

Tumours were grown in animal as described in Example 20. Animals were monitored for tumour growth for 8 to 10 weeks, until tumours were 0.5-1 cm in size. After this time, animals were injected with test article (0.1 ml, 200 MBq/ml) as an intravenous bolus via the tail vein. At various times p.i. animals were euthanased and whole body planar images acquired between 5 minutes and 24 hours p.i. using a gamma camera (Park Medical Isocam-1). Image acquisition times were typically 15-30 min or 150-250K counts (whole body, LEUHR collimator). The uptake of $^{99m}$Tc-labelled CA1-ST$_{5-18}$ in the rat liver metastases model is shown (FIG. 8). The image has the kidneys masked to improve the resolution of the imaged metastases.

Example 22

Uptake of CA1-ST$_{5-18}$ into a Non Colonic Tumour

To examine the specificity of the compounds of the present invention for colonic carcinomas, C57BL/6 mice bearing sub-cutaneous Lewis lung tumours were injected with CA1-ST$_{5-18}$ and dissected at various times p.i. Lewis lung is carcinoma that originally spontaneously arose in the lung of C57BL/6 mice and therefore is not of colorectal origin and is not thought to express the ST receptor.

Example 23

ST Receptor Mediated Uptake of CAT-ST$_{5-18}$

Figure 9:
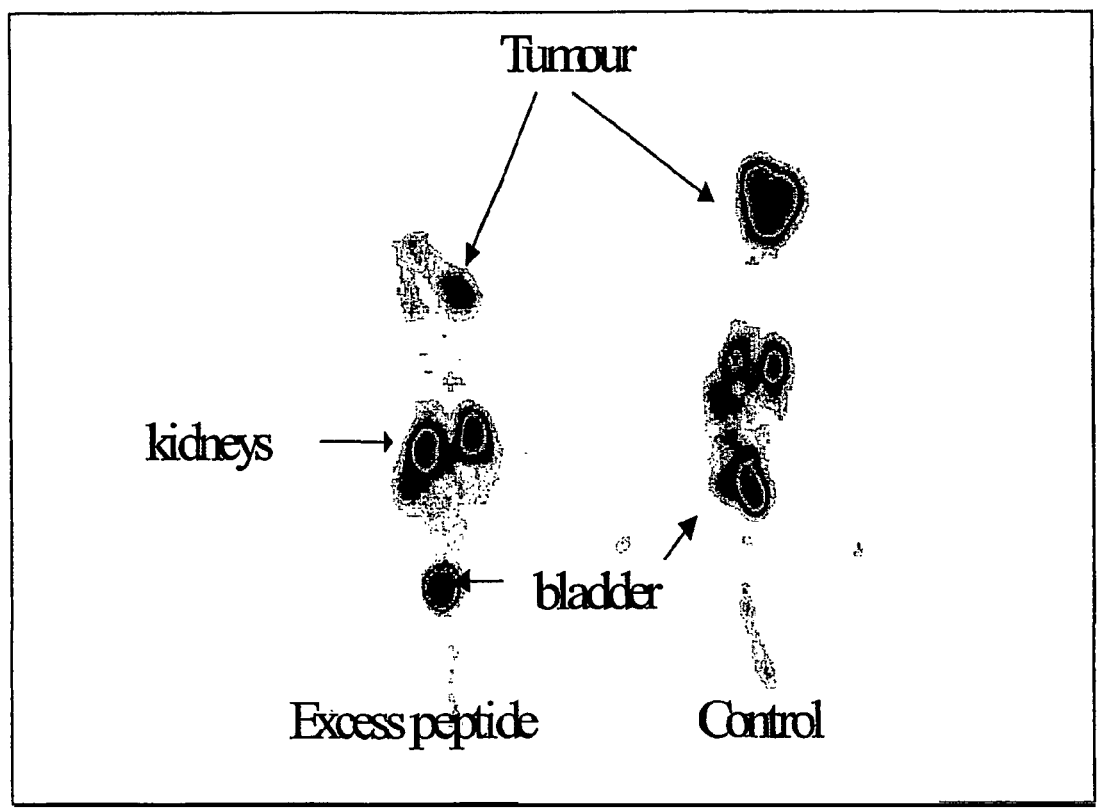
FIG. 9 shows an image of RNU/rnu nude mice bearing T84 liver tumours in the presence and absence of excess peptide. The images are planar posterior static images 120 minutes p.i. of BPLC purified CA1-ST$_{5-18}$ at 20 MBq per animal with LEUHR collimator.

To further examine the specificity of the compounds of the present invention for colonic carcinomas, nude mice bearing T84 tumours as described in Example 17 were imaged. Co-injection of 100 µg/mouse of ST peptide injected with CA1-ST$_{5-18}$ reduced the uptake by 40%. (FIG. 9).

Example 24

Effect of Impurities

It was observed that there was an increase in background tissue activity observed with non-HPLC purified preparations; this could be potentially due to several factors: presence of excess peptide, presence of $^{99m}$Tc labelled impurities (e.g. RHT or others). Further studies were carried out to investigate the other possible causes for the increased background seen with non-HPLC purified preparations, different approaches to reduce impurities such us RHT were tested. Preparations were either filtered (0.2 µm filter size) or had MDP added, known to reduce RHT levels.

Example 25

Comparison of Tumour Model Used with Human Tissue

Figure 10:
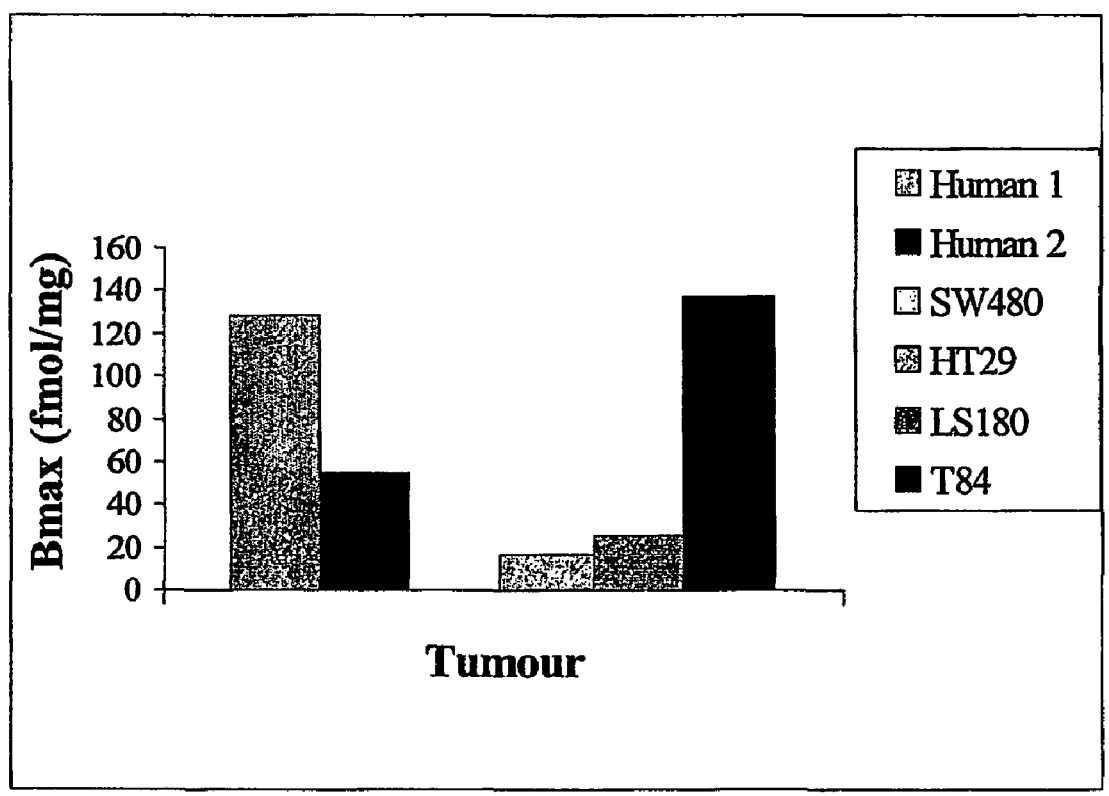
FIG. 10 shows the receptor density (RD) of two human and four xenograft human cell line CRC tumours (nd=receptor density data not detected).

T84 receptor density data show good comparison with those of human liver metastases (FIG. 10). Direct comparison of human liver metastases and xenograft tumour receptor density (Bmax) data clearly show that mean receptor density of human tumours lies in between that seen for T84 and LS180 tumours.

In order to determine whether uptake varied with differences in receptor density, biodistribution studies were undertaken in a range of xenograft tumours with different ST receptor expressions.

It is apparent that many modifications and variations of the invention as hereinabove set forth may be made without departing from the spirit and scope thereof. The specific embodiments described are given by way of example only, and the invention is limited only by the terms of the appended claims.

The invention claimed is:

1. A peptide-chelate conjugate comprising a peptide of SEQ ID Nos. 1 to 7 having affinity for the ST receptor conjugated to a tetradentate chelating agent, where the tetradentate chelating agent is chosen from diaminedioximes and $N_3S$ ligands.

2. The peptide-chelate conjugate of claim 1 wherein the tetradentate chelating agent is of formula A:

(A)

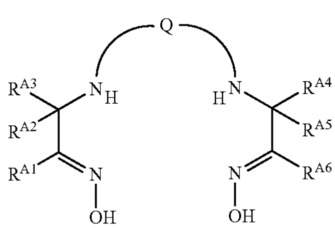

Wherein $R^{A1}$-$R^{A6}$ are all $CH_3$ and Q is —$(CH_2)_2NR(CH_2)_2$— and wherein R is H or $C_{1-10}$ alkyl, alkylaryl, alkoxyalkyl, hydroxyalkyl, fluoroalkyl, aminoalkyl, or carboxyalkyl.

3. The peptide-chelate conjugate of claim 1 where the tetradentate chelating agent is of formula B:

(B)

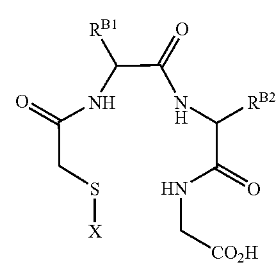

where $R^{B1}$ and $R^{B2}$ are both H and X is a thiol protecting group.

4. The peptide-chelate conjugate of claim 1 where the conjugation is either at the N-terminus or at the C-terminus of the peptide.

5. The peptide-chelate conjugate of claim 1 which further comprises a linker group between the peptide and the tetradentate chelating agent.

6. The peptide-chelate conjugate of claim 5 where the linker group comprises a peptide sequence of 5 to 9 amino acids.

7. The peptide-chelate conjugate of claim 5 where the linker group is selected from -poly-Lys-, -poly-Glu-, -(Gly)$_2$-Glu-(Lys)$_3$-, (Gly)$_2$-Glu-Lys-Glu-Lys-, (Phe)$_2$-(CH$_2$)$_5$—, (Lys)$_6$-Gly-, -(Gly)$_3$-(DGlu)$_3$- and -(Gly)$_3$-(aminocaproic acid)$_2$-.

8. A metal complex which comprises a radiometal complexed to the tetradentate chelating agent of the peptide-chelate conjugate of claim 1.

9. The metal complex of claim 8 where the radiometal is chosen from $^{64}$Cu, $^{65}$Cu and $^{99m}$Tc.

10. The metal complex of claim 8 where the radiometal is $^{99m}$Tc.

11. A radiopharmaceutical composition in a form suitable for human administration, which comprises the metal complex of claim 8.

12. The radiopharmaceutical composition of claim 11, where the radiometal is $^{99m}$Tc.

13. A kit for the preparation of the radiopharmaceutical composition of claim 11 which comprises a vial containing:
 i) the peptide-chelate conjugate of claim 1; and,
 ii) a pharmaceutically acceptable reducing agent.

14. The kit of claim 13 where the reducing agent is a stannous salt.

15. The kit of claim 13 further comprising one or more of stabilisers; antioxidants; bulking agents for lyophilisation; and solubilisers.

* * * * *

UNITED STATES PATENT AND TRADEMARK OFFICE
CERTIFICATE OF CORRECTION

PATENT NO. : 7,608,242 B2
APPLICATION NO. : 10/469801
DATED : October 27, 2009
INVENTOR(S) : Cuthbertson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1355 days.

Signed and Sealed this

Twelfth Day of October, 2010

David J. Kappos
*Director of the United States Patent and Trademark Office*